(12) United States Patent
Valles et al.

(10) Patent No.: US 7,919,302 B1
(45) Date of Patent: Apr. 5, 2011

(54) SOLENOPSIS INVICTA VIRUS

(75) Inventors: Steven M. Valles, Gainesville, FL (US); Charles A. Strong, Gainesville, FL (US); Yoshifumi Hashimoto, Ithaca, NY (US)

(73) Assignee: The United States of America as represented by the Secretary of the Agriculture, Washington, DC (US)

( * ) Notice: Subject to any disclaimer, the term of this patent is extended or adjusted under 35 U.S.C. 154(b) by 145 days.

(21) Appl. No.: 12/113,432

(22) Filed: May 1, 2008

Related U.S. Application Data

(60) Provisional application No. 60/927,114, filed on May 1, 2007.

(51) Int. Cl.
 C12N 7/00 (2006.01)
 A61K 35/00 (2006.01)
(52) U.S. Cl. .................................. 435/235.1; 424/93.1
(58) Field of Classification Search .................. None
 See application file for complete search history.

(56) References Cited

U.S. PATENT DOCUMENTS 7,332,176 B1 2/2008 Valles et al.

OTHER PUBLICATIONS

Valles, Steven et al., "*Solenopsis invicta* virus-1A (Sinv-1A): Distinct species or genotype of SINV-1?," Journal of Invertbrate Pathology, 2005, vol. 88, pp. 232-237.
Valles, Steven et al., "A picorna-like virus from the red imported fire ant, *Solenopis invicta*: initial discovery, genome sequence, and Characterization," Virology, 2004, (continued) vol. 328, pp. 151-157.
Wang, John et al., "An annotated cDNA library and microarray for large-scale gene-expression studies in the ant *Solenopsis invicta*," Genome Biology, 2007, pp. 1-31.
Valles et al., "A new positive-strand RNA virus with unique genome characteristics from the red imported fire ant, *Solenopsis invicta*," Virology, vol. 365, pp. 457-463.

*Primary Examiner* — Bao Li
(74) *Attorney, Agent, or Firm* — John D. Fado; Gail E. Poulos

(57) ABSTRACT

A Unique *Solenopsis invicta* viruse (SINV2) have been identified and its genome sequenced. Oligonucleotide primers have been developed using the isolated nucleic acid sequences of the SINV2. The virus is used as a biocontrol agent for control of fire ants.

5 Claims, 16 Drawing Sheets

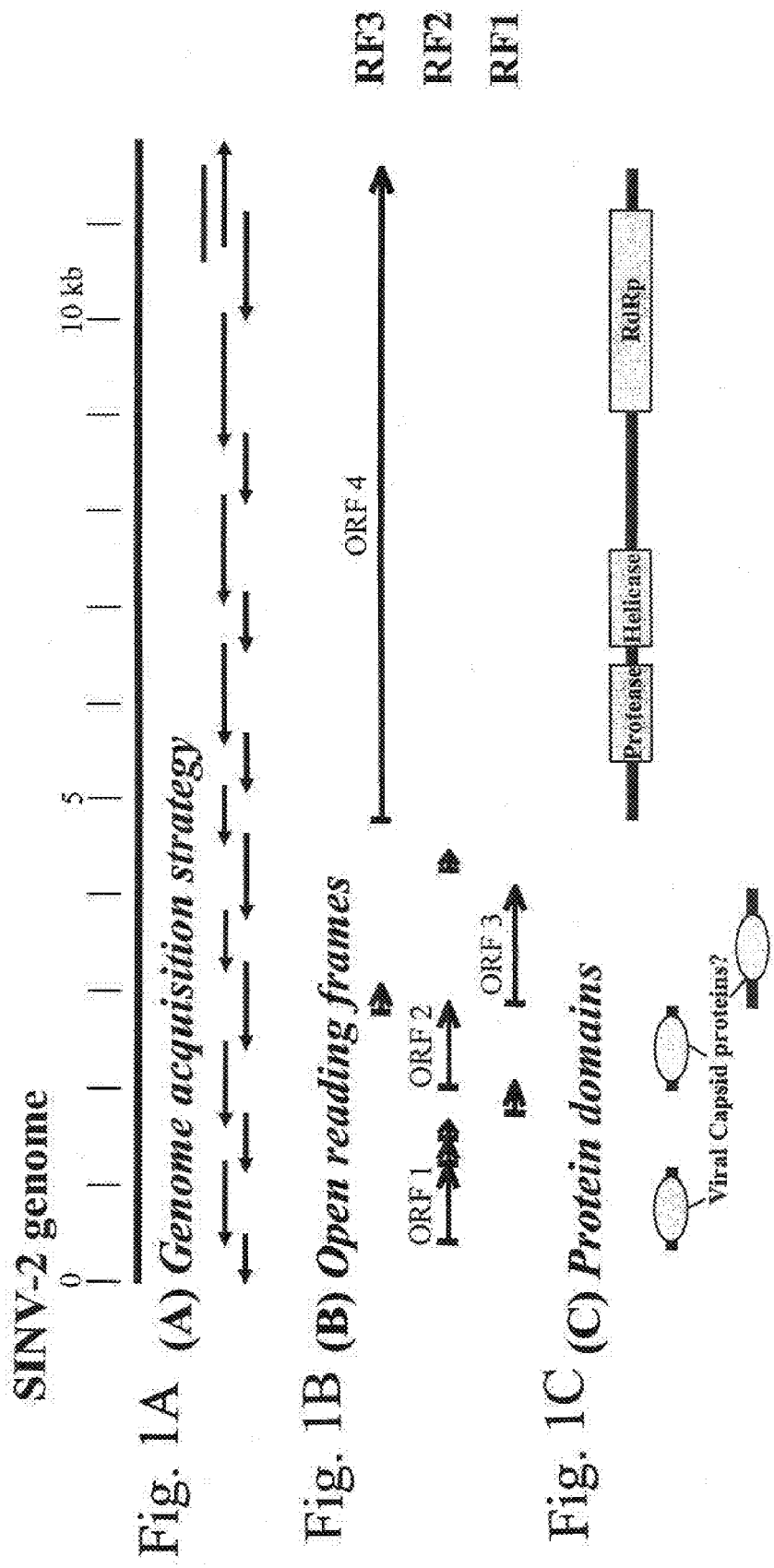

From gb-admin@ncbi.nlm.nih.gov

===================> bankit883385

Fig. 6A

Submission 1 of a total of 1 submission(s).

Comment: This is a new virus described from the host, Solenopsis invicta (ant).

--You have requested a release date of 5/1/2007--

```
LOCUS       bankit883385            11319 bp    RNA     linear       08-FEB-2007
DEFINITION  Complete genome of Solenopsis invicta virus 2 (SINV-2).
ACCESSION   883385
VERSION
KEYWORDS    .
SOURCE      Solenopsis invicta virus 2
  ORGANISM  Solenopsis invicta virus 2
            Unclassified.
REFERENCE   1  (bases 1 to 11319)
  AUTHORS   Valles,S.M., Strong,C.A. and Hashimoto,Y.
  TITLE     A New Single-stranded RNA Virus with Unique Genome Characteristics
            from the Red Imported Fire Ant, Solenopsis invicta
  JOURNAL   Unpublished
REFERENCE   2  (bases 1 to 11319)
  AUTHORS   Valles,S.M., Strong,C.A. and Hashimoto,Y.
  TITLE     Direct Submission
  JOURNAL   Submitted (08-FEB-2007) IFAHI/CMAVE, USDA-ARS, 1600 SW 23rd Drive,
            Gainesville, FL 32608, USA
COMMENT     Bankit Comment: This is a new virus described from the host,
            Solenopsis invicta (ant).
FEATURES             Location/Qualifiers
     source          1..11319
                     /organism="Solenopsis invicta virus 2"
                     /mol_type="genomic RNA"
                     /isolate="From the fire ant, Solenopsis invicta"
                     /specific_host="Solenopsis invicta"
                     /country="USA"
                     /note="ssRNA virus, positive-stranded RNA virus"
     gene            302..1078
                     /gene="ORF 1"
     CDS             302..1078
                     /gene="ORF 1"
                     /note="Contains putative viral coat proteins [intronless
                     gene]"
                     /codon_start=1
                     /protein_id="PROT_1_bankit883385"
                     /translation="MEPQEQQKNEVISRAKEIDTGAVPLPMSNVILGLPYKPDPTTVD
                     KTGVMSRPWSFADLVSQKRIVADLHIDNTTNGKVWEFHNTWMNVLNTIFKTTGSTAGE
```

```
EHLRNLFGLKSWTLNFTFQFRSNFQQVGQLIIFYTNMPRLLKNYHSATDVTEDYYSSY
MVQTQLPHRKIPMGEDQDVDVSLKWISPHAAAFGSDMYADGQTVYDYTSYLYDMGTLR
                    LHVPFPMEVATGVDSAMTVRVWTWLSDLATGAYKPYDSVL"   SEQ ID NO: 67
     gene            1829..2647
                     /gene="ORF 2"
     CDS             1829..2647
                     /gene="ORF 2"
                     /note="Contains putative viral coat proteins
[intronless
                     gene]"
                     /codon_start=1
                     /protein_id="PROT_2_bankit883385"

/translation="MQDKQLRLIMSTQQMLSFNPPRLVNVPQQPPPQTVSMTLEHSGV

PVDEPLLVTDIPPDFQWMAQLQRYHTSFVVSKNKNPKDPLWRDNVHTMVETSDGDPYK

IIPSWNLLPMVTSRWWNGVISYKLIAIKPPRVTGKLLIRYSFDPHDDFSGDSVRRGIC

KEWDLGQSSECEFDVVATNTIRARPTWLPLIRSGNVTGAYWLDQYLPYQTWHYGSLMI

ELAQRIQVGSIFPDSIRILVFKCFKNAEFYLPTDARGDSPHFLATGTVPSGRKA"    SEQ ID NO: 68
     gene            2644..3792
                     /gene="ORF 3"
     CDS             2644..3792
                     /gene="ORF 3"
                     /note="Contains putative viral coat proteins
[intronless
                     gene]"
                     /codon_start=1
                     /protein_id="PROT_3_bankit883385"

/translation="MNAEEPIQSVGANQIVGTQGDPLQEQPQVPTTAMPRQMSFSSLI

YQWQPMGLRVVVNLPFVGDDKDFLFYIRNGPFIPYPCKYRDDSISQEPGVSLYPAWVM

SYGLNNMAAVFLFSDSFREYPDYNGTKNFPITLTQYDTPPIISSMAMSFRRWRGAMQY

RIRVVAGSITQGYIIVTPLKNIFVPIAIYNQFKYQPAIQRQDHSYKASMMNSYGLVDI

AMIRHSEITMPFDYPVAYYDQFAWMSRRVSPSQDWAGISDVSKLKPVPVGPTLKSEPH

GDNPIAVGLRGALSASAVGSQLEFELEYRCMEGFQFADPYLPPRRLCADTRNYLKNGR
                    LPYRIPSREWESDGIGEPTKVKKQSRLTEVVTGTAGINLGKSSRAHYG"SEQ ID NO: 69
     gene            4455..10916
                     /gene="ORF 4"
     CDS             4455..10916
                     /gene="ORF 4"
                     /note="Contains putative helicase and RNA-
dependent RNA
                     polymerase [intronless gene]"
                     /codon_start=1
                     /protein_id="PROT_4_bankit883385"

/translation="MASSSSSSNLQPRRKFQLRDEIKCALARFKHQQSEGWRIHLEKS
```

```
KLASLVKMYTERYLYVKGMPFEPVEFHRVELLEYLRALPLPEEKETATGRRLAQQPVF
GVPDIPIYYYNYKVPKVTPVDLKSMVNHYQCQEHIHKREESHHPDGLGWGGGTDSTIE
CVIDVYSCLLRTHAVKTAYIKLLDILKGDKFSNLTSEGILFACLHLIIRGVAGSAICK
NHSEWRQEQYTQDQLWKYTKDFQNGVPPQHIIGQYMRETLYHQLMVTEETKAMRISSS
KHDHTKFRPYSVYWYTWYWGIFQKMSKQNQRMVELGVDMSDPEISSHPTMFNISKSMG
ESFMEGALSSPEFNQVLNLSRTLPEEVATKIDQVTKEREDSLKESAREILTEFKTSMH
DLAEETLDKLVMKSKDIGQVLTEAVEPFVAVLESLQSLAENAISQINGFLKPMEGFSG
INLSVTSILECLKYYIVYINTETTSLKMILVLLMMNALGITSKLFSWMLEFWRMYSSS
ELEGHTVDAEPTSFLDWLVNAPTKFMVLLGATFASMAKGAKLSTSEFFKLAKDLSDKM
RSIHFISMGVAAFERLFDYGVRFWKFISEWISTHIFGRTPDRVTMARKVMKLILKIKY
FNTEAGLNAVRMAENVRVEAEKLFPEWNALLAQCRDNPEYRQMYQDLERQTRAVKEVS
DFVTRFRAVSNFQPTMFHVQLVGRPGIGKSTLIKTMTADLTRSLWPSEPKPSFYSMNM
NLEFFDGYAGQRIMIADDVYKMNEPKHLTATIGLITNTPVILPMANLADKGVQLTSEV
FLSTTNTAYPLGKDVLCMEAVHRRRHMLVDVTCDERVIEEGSGQFSEALFRQYYPGQD
KSKFPHLKFGLMKPVPKVFGGAAETVLVGEDEQIVYNEYAKLLRDANFKVSLGHKELD
PTFYFNEENLPQGFSYPARGWSYEQFMTNCMVRFRSFRGMEESYSTAVKYAHTATCLA
EIDALLDQNSDCDGPEIPTGVGRFDLIKMYGKECMHPMGTDDPLGKRIASDIDAHRAT
APELEHFDLDAWVEKTLDGYIGRNEKPTGITLEEESIRRTTILRRRKKAIVPPQLQEA
LKVHRHNLDWYIRIHDHPTTWDSCVFEGKNLEVEMLQAVMMQALSRVVPTRAAFGELV
SEDKPESNVWWRWFRRLATIPGLAVDAYATYNQVIRLLLPSENLVWPEGFGSRTGYMS
DMSIAFLQRLEKINGEWCLNVTDLHSIFPSPCVAKVYSNGLTQETYEIPVDIAFWLSH
AQHFRIFLNRFCNFTAEQQQTLVDEAHFRNRFTGTYTYEYFAKQAEGTLKGTVYAALS
YLTKPYKYLAVRFPQITITATYILAVTAVVFIVKSIASLFSHPTSKVLHRGPVSNIVY
RGNYPTSQRLPELSTTILKRNVANICISTTMESRKAQCLRTEQFVLCNSHIFDGLVPD
GGQYLVTLTDGSLTNDFWVPETQVYIDKDRDLAIIFSRLFPAVRKISDHFIKQSDYER
SEFTGQMVICSKTPEYGIVEHYPVVGKVDRLDLKGITRPAVLTQVMMLNGSTVSGRSG
SPVIAQVNGLARLIGIQSWAMDTLYQPKVAVQTVTAELFEELVKNVSAQSEDLLVRRI
AEPEYGECYPTHAFASVPEFMLACEDEHVVGDVGMNKIKPSFISNHLTAAGITTKRIP
```

AVMSDRDPRLPRDSRHPLEHSLGKYYRGKVNPIPHNIINRAKDYIIKYYKGRLDTKNF
AALTIEEAITGTREDGSNPMNLKSSPGIPFIFDKRERKGKKDYMEIDEFGEVDHIDPE
FLQGYYKFEDSLSKGEVPYTRAYDFPKDELRPINKVLGDETTPPKTRSVTCMNVYYIL
AWRRYTMRFWSAMHRAADGTSMFGPGINPEGPEWSALYHHLNRHPNAVDFDVSNWDGF
LFAQLFYAVLDIIKAIMNVKKGTPVDYILTSIFFDVMNCFIQFLNIIYQKSRGIISGF
PGTAEVNTLAHILLIVCIYLMLVAKTIWDSFEMFLRMVSAILYGDDILLTIHDDILHL
FNGKTIQREYERLGYTVTSATKSSEIVEAKPLSQCQFLKSSWRQLLPGYYIRVLDLEV
AYDLVHWVRAKQHPRGQFFQNYMDALWICFGHGQQVFESFQLTVNQILTKFSEDNIVF
SYKDFEDDYFARYLPNFKFNL"

Fig. 6D

```
BASE COUNT     3171 a   2276 c   2606 g   3266 t
ORIGIN
        1 ttttaaatag atcgcatata cagactcctg tatagggagg gcatcattgg
tcggcatggt
       61 aaagcatggg ctgtggtgtc ttatcagcgg agggcagtat tggtcggcat
ggtaaagcat
      121 gggctgtatt gtcttatcgt tgcgaaatga cgtttaaata ggctgatata
cccgaatgta
      181 tatccctcct ttcttttttct atcttgtagt tttaagttag ttttagttag
catgaggcgg
      241 tgctccggcg gaattatgta gaggaccatc gtttattgca caactgtacc
tgattatttt
      301 aatggaaccg caagaacaac aaaagaacga agttatttcg agggcaaagg
agatcgatac
      361 tggagcagtt ccactaccga tgtccaatgt catcttagga ttaccttata
aaccagaccc
      421 gaccactgtg gataaaaccg gagtgatgag caggccgtgg agtttcgcgg
atcttgtgtc
      481 tcagaagcgg atagttgctg atttgcacat tgataatacg actaatggaa
aagtctggga
      541 gtttcataac acctggatga atgtcttgaa tacgatcttt aagacaactg
gtagtactgc
      601 tggcgaggaa catctccgca atttgttcgg cttaaaatcg tggacgttga
atttcacgtt
      661 tcaatttcgt tcaaattttc agcaggttgg tcaactaata atctttttata
ccaacatgcc
      721 gaggttgctt aagaattacc attcagcaac cgatgtcacc gaagattatt
actccagtta
      781 catggtgcag acacagcttc cgcataggaa aattccgatg ggcgaggacc
aagatgtgga
      841 tgtctcattg aaatggattt caccgcatgc tgctgctttt ggtagtgaca
tgtatgctga
      901 tggacagact gtctatgatt atacaagtta tttgtatgac atgggcactt
tgagactcca
      961 tgtgccgttt ccaatggagg ttgcgacagg tgttgactca gcaatgacag
tccgtgtttg
     1021 gacgtggttg tctgacttag caactggagc gtataaacca tatgattctg
ttttatgaat
     1081 ggactcccta ccaccgcaac tcaatttact aattggtaca gtgagaactt
tgcttcttct
```

Fig. 6E

```
1141 gggatatctt tccttgcaag tggcggcgca aattgagtcc ctggcagtag
cagtgtttcg
1201 tcctctgtta cgccgagtcg ggtacaacct gctagactca atcaggacta
tgccagcttc
1261 gcacagtcat ctcccgctaa caatcaagga tttgacccat ggggagtgaa
ggactcgcca
1321 attattgatg atgacgaacg tgttcaatct aatttggaaa ctgagacaga
aataccgaat
1381 gaagctgagg aagggttatc agagactgtt gaggcagttg gtgaggttac
gactggagtt
1441 gaggcagctg aggcgaccgc tgcggtgtcc actccttgga ccttgctggc
tatagccaat
1501 caacaactag gccaagcagt tagtacagca catgtgtcag gattgcaaca
gcaatcctcg
1561 gcggattaca cggccaatat gcagtctcac ggcttgaatg taggtcttaa
tgcagatctt
1621 attcgtgaac agcagagcca gaccatttcg aggcagcagg caggaggttc
tattgggtct
1681 ttgcttgggc cccttggaac gttgatcgga caggccattg ccggatataa
ctctgtgaac
1741 caagaggatt tgaaaacagc cgcttctttc aacggctatg ttaatcccca
aatgagtaac
1801 atcgttgctt cgcagacaac atctggtgat gcaggacaag caactcaggt
tgataatgtc
1861 gacacaacaa atgcttagtt ttaacccacc acggctagtg aatgtgcctc
aacagccacc
1921 tccacaaacc gtgagtatga ccttagaaca ctccggtgtt cctgttgacg
aaccgctttt
1981 agtcacggat atccccctg attttcagtg gatggcccag ctacaacgtt
atcataccctc
2041 gtttgtagta tctaagaata agaatcctaa ggatcccttg tggcgtgaca
atgttcacac
2101 catggttgag acttctgatg gtgatccata caagatcatt ccatcatgga
atttgttacc
2161 aatggtgact tccaggtggt ggaatggggt tatcagctac aaactcattg
ctattaagcc
2221 accacgagtt actggaaaat tgttgataag gtactcattt gacccacacg
atgacttctc
2281 tggtgactca gttcgccgtg ggatttgtaa ggagtgggac ctcggacaat
catctgagtg
2341 cgaatttgat gtagttgcta caaatacaat tcgtgcccga cccacatggt
tacccttgat
2401 acgatctggt aatgttactg gagcctactg gctggaccaa tatttgccat
atcaaacatg
2461 gcattatggt tcactcatga tagaactggc ccagcgaatt caagttggat
caatctttcc
2521 tgattctata cggatattgg tattcaaatg ttttaaaaat gcagagttct
acctgcccac
2581 tgatgcgaga ggggattccc cgcatttctt ggccactgga actgtgcctt
caggtcgaaa
2641 ggcatgaacg cagaggaacc tattcaatct gttggggcca accaaatagt
tggaactcaa
2701 ggagatcctt tgcaagaaca accacaagtc cccactacgg ctatgccacg
ccaaatgtca
2761 tttcatcat tgatatatca gtggcaaccg atgggcttga gagtggttgt
taatttgcct
```

```
2821 tttgtaggag atgacaaaga ctttctgttt tatatacgta atggcccttt
tattccttac
2881 ccgtgcaagt accgagacga tagtatttcg caagagcctg gcgtcagtct
atatccggcc
2941 tgggtcatgt catatggcct gaataatatg gcagcagttt ttctatttag
tgactccttt
3001 agagagtatc ccgactataa tggaacaaaa aattttccaa ttactttgac
tcaatatgat
3061 actccaccta ttatatcatc aatggccatg tcctttagaa gatggagagg
tgccatgcaa
3121 taccgcattc gtgttgttgc tggttccatt actcagggtt atatcattgt
gacccccgttg
3181 aagaacatct ttgtgcctat tgccatctat aaccagttta agtatcaacc
ggcaatccag
3241 cgtcaggatc actcatataa agcatctatg atgaactcat atggactggt
tgatatagct
3301 atgattaggc actctgaaat cactatgccg tttgactatc cagtagcata
ttatgatcaa
3361 tttgcatgga tgtcaaggcg ggtttcacca tcacaggatt gggctggcat
ttcggacgtg
3421 tcgaaattaa agcctgttcc agtgggacca actttaaaat cagaaccaca
tggtgacaat
3481 tttatagcag ttggtcttcg cggtgcactg tctgcttctg cagtgggatc
acaactcgag
3541 tttgagctgg aataccgctg tatggagggg tttcagtttg cggaccctta
tttaccgcca
3601 cgcagattat gtgccgatac ccgcaattat cttaagaatg gacgtcttcc
ctaccgaata
3661 ccatcaaggg aatgggaatc ggacggcata ggtgaaccaa ccaaggtcaa
gaaacaatct
3721 cgcttgaccg aggttgtaac tggtacagct ggaatcaatt taggtaaatc
ttccgggcc
3781 cattatgggt aaccttttga tgtttaaatt ttaattccgt tctcgccgga
gatgagtacc
3841 ggtttgagtt taattccagg gtagcgcgag ccgtgagtca gcccagacaa
gcgcagtagc
3901 cctacttgga gaggttctcc ttgagcgacc agaagctggc attgaatcga
gtcacataat
3961 gctgagagta gagggatttg cattctattg tgaaagcaat aatttgagag
ttaagcccat
4021 cacattgtgc actcggaata ttgtgcagcg cgaaaggtta gtaacattaa
gttggcgaaa
4081 ggttagcgca gcaatgattg gtggtaacgc tggatcttat tgtggaagca
atggatgaat
4141 atgaagttga aatcaggatc accacacccc cgcagcatag cggtaccgta
ctgaatgtca
4201 caatccagtg atgattcgaa gcctataacg ggcggacgtg tttaaatggt
gttttatgtg
4261 gatgttagtt cgccggaatg tgcagctccg gatatcgagt cgaagattca
gtgaccagtg
4321 gagcaagcaa cataggtaac tatttcgtat gattttactc acaaaattgc
actgggcagg
4381 agcttccaaa ggaaccttct gcttctcgta actgcacaca aactagattt
cttattttcg
4441 gagagcatat caaaatggct tcaagttcaa gttcaagtaa tttgcaacct
cgcaggaagt
```

```
4501 ttcaactccg cgacgaaatt aagtgtgcac ttgctcggtt taaacatcaa
cagagtgagg
4561 ggtggagaat acacctggaa aagagcaaac tcgcatcatt ggtcaagatg
tacacggaac
4621 gttatctata cgtgaaaggt atgccttttg aacctgtgga attccatcga
gttgagttgc
4681 tcgaatatct tagggccctc ccattaccgg aggagaagga aacggcaaca
gggagacgtc
4741 ttgcacaaca gcccgtgttt ggcgttcccg acatacctat ctattattat
aattataagg
4801 ttcctaaggt cactccagtt gaccttaaga gtatggtgaa tcattaccag
tgccaagaac
4861 atatccataa gagagaagaa tcccaccatc ctgacggact tggttggggt
ggtggaacag
4921 attctactat agagtgtgta atagatgttt attcatgtct gttgcgtaca
catgctgtaa
4981 aaactgcata cataaagctt ttggatattc ttaaagggga taaattttcc
aacctgacat
5041 ctgagggaat tctttttgct tgtctacatc ttattattcg aggagttgct
ggatcagcaa
5101 tatgtaagaa ccattcagaa tggagacagg aacagtacac acaagatcaa
ctgtggaagt
5161 atactaagga ttttcaaaat ggtgttcctc ctcagcacat aattggtcag
tatatgcgcg
5221 aaaccttgta ccatcaactg atggttaccg aggaaacaaa agccatgcgc
atttcatcat
5281 ctaaacatga ccacacaaaa ttcagaccgt actctgtata ttggtatacc
tggtattggg
5341 gaattttcca gaaaatgagt aagcagaatc aacgaatggt tgagttggga
gttgatatga
5401 gtgatcccga gatttctagt cacccccacaa tgtttaacat ctccaaatct
atgggtgaga
5461 gcttcatgga aggtgcattg tcatcgcctg agtttaatca agtcttgaac
ttgagcagaa
5521 cccttcctga agaagtagca acgaaaattg atcaagtaac caaggaacgt
gaggattctc
5581 ttaaagaatc tgcacgcgaa attttaacag aattcaaaac tagtatgcat
gatttggctg
5641 aggaaacact tgacaagctg gttatgaagt ccaaggacat tggacaagtc
ctaactgaag
5701 ctgttgagcc atttgtggcg gttcttgaat cactgcaatc cttggctgaa
aacgccatat
5761 cacaaattaa cggattttta aaacccatgg aaggtttctc aggaataaat
ttgtctgtca
5821 catcaatttt ggagtgtctt aaatattata ttgtttatat taatacagaa
accacatcct
5881 tgaagatgat tctagtttta ttgatgatga atgctttagg tataacatca
aagttatttt
5941 cctggatgtt ggagttttgg agaatgtatt catcatccga actcgaagga
catacagttg
6001 atgctgaacc cacgagtttt ctggactggc tggtaaatgc gccaaccaag
ttcatggtgc
6061 tcttgggtgc tacctttgca tctatggcga agggagcaaa gctctcaaca
tctgagttct
6121 ttaagctggc taaagattta tctgataaga tgaggtctat tcattttatt
tccatgggag
```

Fig. 6H

```
6181 ttgccgcttt tgagcgcctg tttgattatg gggttcgatt ctggaagttt
atctcggagt
6241 ggatttctac acacatattt ggtcgtacac ctgaccgagt tacaatggca
cgtaaagtga
6301 tgaagttgat tttgaaaata aaatacttca atactgaggc tggattgaat
gctgtaagaa
6361 tggctgagaa tgtaagagtt gaggctgaaa agctatttcc ggaatggaat
gcattgctag
6421 cgcaatgccg tgacaatcct gaatatcgtc agatgtatca ggatttggag
cggcagacac
6481 gcgcagttaa agaagttagc gactttgtca ctcgcttccg tgcagtttcc
aatttccaac
6541 cgacgatgtt ccatgttcag ctagtgggac ggccaggaat tggtaagtct
actttaatta
6601 agactatgac agctgatttg actcgatcgt tgtggccatc tgaaccaaaa
ccatcattct
6661 acagtatgaa tatgaacttg gaattctttg atgggtatgc aggacagcgc
ataatgattg
6721 cggatgacgt gtacaagatg aatgagccta agcatttaac agcaacgata
ggccttataa
6781 cgaatacacc tgttatattg ccgatggcaa atctggctga taagggagtg
cagcttacaa
6841 gtgaagtttt cttatcgacc acaaatactg cctatccatt gggcaaggat
gttttgtgta
6901 tggaagcagt tcacaggaga cgtcatatgc tcgttgatgt aacatgtgac
gagcgtgtaa
6961 tcgaggaggg tagtggacag ttttcagaag cactattccg acaatattat
cctggacaag
7021 ataaatccaa gttcccacat cttaagttcg gccttatgaa gcctgtgcct
aaagtgtttg
7081 gaggagctgc ggagaccgtt ctcgttggag aagatgagca gattgtttac
aacgagtatg
7141 caaagttgct cagggatgca aatttcaaag tatccttggg tcataaggaa
ttagatccaa
7201 cattttattt caatgaagag aatttgccgc aaggattttc gtatcctgcg
cgtggttgga
7261 gttatgaaca gtttatgacc aattgcatgg ttagattccg ttcctttaga
ggaatggagg
7321 aaagctatag tacggctgtc aagtatgcac acactgcaac ttgcctagct
gagattgatg
7381 cattgctgga tcagaattct gactgtgatg ccctgaaat accaactgga
gttggccgct
7441 ttgatttgat taaaatgtat ggaaaagagt gtatgcatcc catgggaaca
gatgatcctc
7501 tggggaagcg tattgcttct gatattgatg cccatagagc tactgcacct
gagctagaac
7561 actttgatct tgatgcttgg gttgagaaga ccttggatgg atatattggt
agaaatgaaa
7621 agcctactgg catcactctt gaggaagaaa gtatacggcg tactactatc
ttgcgcagaa
7681 gaaagaaggc tattgttccc ccgcagttgc aagaagccct gaaagttcac
cgacataatt
7741 tggattggta catcaggatc catgatcatc ccacaacgtg ggattcttgt
gtgtttgaag
7801 gcaagaattt ggaggttgaa atgttgcaag cagtgatgat gcaggcatta
tcacgtgttg
```

```
7861 taccaactag agcagcattc ggcgagctag tatcagaaga taagcctgaa
tctaatgtgt
7921 ggtggagatg gtttcgccgt cttgccacta ttccaggcct tgccgtagat
gcatacgcaa
7981 catacaacca agtgattcgc cttctattgc catctgagaa tttggtgtgg
cctgagggct
8041 ttggatctag aaccggctat atgtcggata tgtccattgc cttcttgcag
cgtctagaga
8101 aaatcaatgg agaatggtgc ctgaatgtga cggatttgca ttcaatcttt
ccgtcaccat
8161 gtgttgcaaa ggtctactca aatggactga ctcaggaaac atatgaaatt
cctgtggata
8221 tagcttttg gctatctcat gcacagcatt tcagaatatt cctgaataga
ttctgcaatt
8281 ttacagctga acaacagcag actcttgtgg atgaagcaca tttcaggaac
cgctttaccg
8341 gaacatacac ctatgagtat tttgctaagc aggcagaagg aacgctgaag
ggaacggttt
8401 atgcggcact gtcgtatctc acaaagccat ataagtatct ggctgtgaga
tttccacaaa
8461 tcactatcac tgcaacctac atccttgcag tcacagcagt ggtgttcatt
gttaaatcaa
8521 ttgcatcact gttctcccat cctacctcga aggtcttgca tcgtggtcct
gttagtaata
8581 tagtgtatcg cggaaattac ccaacatcac aacgattgcc tgagctatca
actaccatct
8641 tgaagagaaa tgttgctaat atttgtatat caacaactat ggagtccaga
aaggctcagt
8701 gtctccgtac ggagcagttc gtcttatgta ttcgcacat atttgacggg
cttgtcccag
8761 atgggggcca atacttggta acattaactg atggctcatt gactaacgat
ttctgggttc
8821 ctgagaccca agtgtacata gataaagatc gtgatttagc aatcatattc
tcgcgactat
8881 tcccagcagt gcggaaaata tcagaccatt tcattaagca gtctgattat
gagcggagtg
8941 aatttacggg acagatggta atctgctcaa aaacacctga gtatggaatt
gtagaacatt
9001 atccagttgt tggcaaggtt gatcgccttg acctcaaagg aataacacgt
ccagcagtgt
9061 tgacgcaagt tatgatgctt aacggatcca ctgtctccgg aagaagtgga
tcacctgtta
9121 ttgcacaagt gaacggctta gcaagactca ttggcataca gtcttgggct
atggatactt
9181 tataccaacc caaggttgct gttcagactg tgactgctga gctgtttgaa
gaacttgtga
9241 agaatgtttc tgcgcagtcc gaagatctat tggtccggcg tattgctgag
ccagagtatg
9301 gtgaatgcta tccaacacat gcatttgcct cagtacggga attcatgctt
gcttgtgaag
9361 atgagcatgt tgttggagat gtaggaatga acaaaattaa accatcattc
atttcaaatc
9421 acttgacagc tgcaggaatt accacgaaac gtattccagc ggtcatgtct
gataggatc
9481 cccgtttgcc tcgggattcc cgtcatccgt tggaacattc tctgggaaaa
tattatagag
```

```
     9541 gcaaagtaaa tcctatcccg cacaatataa tcaaccgggc taaggattat
ataatcaaat
     9601 attataaggg gcgtcttgac accaagaatt ttgctgcact gacaatagaa
gaagcaatta
     9661 cgggcactcg agaggatgga agtaatccca tgaatctcaa gtcatcgcct
ggtatcccgt
     9721 tcatatttga taagcgcgaa cgtaaaggta agaaggacta tatggagatt
gatgaatttg
     9781 gtgaagtgga ccatatagat cctgagtttc ttcaagggta ctacaagttc
gaagattccc
     9841 tttcaaaggg tgaagttcca tatacgcgcg cctatgattt tccaaaagac
gaacttcgcc
     9901 ctataaataa ggttttgggt gatgaaacca caccaccaaa gactagatca
gtaacgtgca
     9961 tgaatgttta ctacattctt gcatggagac gctatacaat gcgtttctgg
agtgctatgc
    10021 accgtgcagc tgacggtact tcaatgtttg gacccggaat taatcctgag
ggtccagaat
    10081 ggtctgctct ttatcatcac ctgaaccgcc atcctaatgc tgtagatttt
gatgtttcca
    10141 attgggatgg ttttctttc gctcaactat tttatgcagt tttagatata
ataaaagcaa
    10201 taatgaacgt aaagaaggga acaccagtag attatatttt aacttctatt
ttctttgatg
    10261 ttatgaattg tttcattcaa tttctaaata ttatctacca gaagagcgt
ggtattatat
    10321 ctggcttccc cggaacggcg gaagttaata ctctggctca tatactctta
atagtatgta
    10381 tttacctgat gcttgtcgca aagactatat gggactcttt tgagatgttt
ttgcgcatgg
    10441 tgtctgccat tttatatggt gatgacatct tacttactat tcatgatgac
atcttgcatc
    10501 tctttaatgg taaaacaata caacgagagt atgagagact aggttacact
gtgacttctg
    10561 ccacgaagtc cagtgagata gtggaagcaa aaccattgtc tcaatgtcag
ttcttaaaat
    10621 ctagctggcg ccaacttctg cccggatatt atatccgagt tttggacttg
gaagtagcct
    10681 acgatctggt tcactgggtc agagcaaagc aacatcctcg tggacagttc
ttccaaaatt
    10741 acatggatgc actgtggatt tgttttggcc acggtcaaca ggttttcgaa
agttttcagc
    10801 tcaccgttaa tcagatttta acgaaatttt ccgaagataa catagttttc
agttacaaag
    10861 attttgaaga cgactatttt gcgcgatatt taccaaattt taaatttaac
ttgtagatag
    10921 ggttttttgga tgtcgtgacg ttagttataa gtatcaccta gcgctagcgc
ctagctggca
    10981 aagtatcccc ttggcttaga gaaaactcac tagatggagg ctcgaagcgg
ctccggttgg
    11041 gcaatgcgtt tacctacgct aatgctttgt atcatcttat tgcatcgacc
tgttgtgtgt
    11101 gtgttgacgt agaacctccg cacagacttc aggctttgta ttcatttca
tttgtctgac
    11161 acctatgtcg cacgatccta ccggggcggc gctgtaaatt gttaatcagt
aatttcaatt
```

```
   11221 tttcaaaatt taattcactg cggactccca taagtccgcc atgatttgtt
ttgttttttct
   11281 aaatttattt catttgttct attaaaaaaa aaaaaaaaa
//
```
SEQ ID NO: 1

Fig. 6K

SEQUENCE LISTING

<160> NUMBER OF SEQ ID NOS: 69

<210> SEQ ID NO 1
<211> LENGTH: 7959
<212> TYPE: DNA
<213> ORGANISM: Solenopsis invicta virus

<400> SEQUENCE: 1

```
ttttaaatag atcgcatata cagactcctg tatagggagg gcatcattgg tcggcatggt      60
aaagcatggg ctgtggtgtc ttatcagcgg agggcagtat tggtcggcat ggtaaagcat     120
gggctgtatt gtcttatcgt tgcgaaatga cgtttaaata ggctgatata cccgaatgta     180
tatccctcct ttcttttttct atcttgtagt tttaagttag ttttagttag catgaggcgg     240
tgctccggcg gaattatgta gaggaccatc gtttattgca caactgtacc tgattatttt     300
aatggaaccg caagaacaac aaaagaacga agttatttcg agggcaaagg agatcgatac     360
tggagcagtt ccactaccga tgtccaatgt catcttagga ttaccttata aaccagaccc     420
gaccactgtg gataaaaccg gagtgatgag caggccgtgg agtttcgcgg atcttgtgtc     480
tcagaagcgg atagttgctg atttgcacat tgataatacg actaatggaa aagtctggga     540
gtttcataac acctggatga atgtcttgaa tacgatcttt aagacaactg gtagtactgc     600
tggcgaggaa catctccgca atttgttcgg cttaaaatcg tggacgttga atttcacgtt     660
tcaatttcgt tcaaatttc agcaggttgg tcaactaata atcttttata ccaacatgcc     720
gaggttgctt aagaattacc attcagcaac cgatgtcacc gaagattatt actccagtta     780
catggtgcag acacagcttc cgcataggaa aattccgatg ggcgaggacc aagatgtgga     840
tgtctcattg aaatggattt caccgcatgc tgctgctttt ggtagtgaca tgtatgctga     900
tggacagact gtctatgatt atacaagtta tttgtatgac atgggcactt tgagactcca     960
tgtgccgttt ccaatggagg ttgcgacagg tgttgactca gcaatgacag tccgtgtttg    1020
gacgtggttg tctgacttag caactggagc gtataaacca tatgattctg ttttatgaat    1080
ggactcccta ccaccgcaac tcaatttact aattggtaca gtgagaactt tgcttcttct    1140
gggatatctt tccttgcaag tggcggcgca cagtgtttcg tcctctgtta cgccgagtcg    1200
ggtacaacct tgccagcttc gcacagtcat ctcccgctaa caatcaagga ggactcgcca    1260
attattgatg atgacgaacg tgttcaatct aataccgaat gaagctgagg aagggttatc    1320
agagactgtt gactggagtt gaggcagctg aggcgaccgc tgcggtgtcc tatagccaat    1380
caacaactag gccaagcagt tagtacagca gcaatcctcg gcggattaca cggccaatat    1440
gcagtctcac tgcagatctt attcgtgaac agcagagcca gaccatttcg tattgggtct    1500
ttgcttgggc cccttggaac gttgatcgga ctctgtgaac caagaggatt tgaaaacagc    1560
cgcttctttc aatgagtaac atcgttgctt cgcagacaac atctggtgat tgataatgtc    1620
gacacaacaa atgcttagtt ttaacccacc aacagccacc tccacaaacc gtgagtatga    1680
```

-continued

```
ccttagaaca aaccgctttt agtcacggat atccccoctg attttcagtg atcatacctc    1740
gtttgtagta tctaagaata agaatcctaa atgttcacac catggttgag acttctgatg    1800
gtgatccata atttgttacc aatggtgact tccaggtggt ggaatggggt ctattaagcc    1860
accacgagtt actggaaaat tgttgataag atgacttctc tggtgactca gttcgccgtg    1920
ggatttgtaa catctgagtg cgaatttgat gtagttgcta caaatacaat taccottgat    1980 acgatctggt aatgttactg gagcctactg atcaaacatg gcattatggt tcactcatga    2040
tagaactggc caatctttcc tgattctata cggatattgg tattcaaatg acctgcccac    2100
tgatgcgaga ggggattccc cgcatttctt caggtcgaaa ggcatgaacg cagaggaacc    2160
tattcaatct tggaactcaa ggagatcctt tgcaagaaca accacaagtc ccaaatgtca    2220
ttttcatcat tgatatatca gtggcaaccg taatttgcct tttgtaggag atgacaaaga    2280
ctttctgttt tatatacgta atggcccttt tattccttac ccgtgcaagt accgagacga    2340
tagtatttcg caagagcctg gcgtcagtct atatccggcc tgggtcatgt catatggcct    2400
gaataatatg gcagcagttt ttctatttag tgactccttt agagagtatc ccgactataa    2460
tggaacaaaa aattttccaa ttactttgac tcaatatgat actccaccta ttatatcatc    2520
aatggccatg tcctttagaa gatggagagg tgccatgcaa taccgcattc gtgttgttgc    2580
tggttccatt actcagggtt atatcattgt gaccccgttg aagaacatct tgtgcctat     2640 tgccatctat aaccagttta agtatcaacc ggcaatccag cgtcaggatc actcatataa    2700
agcatctatg atgaactcat atggactggt tgatatagct atgattaggc actctgaaat    2760
cactatgccg tttgactatc cagtagcata ttatgatcaa tttgcatgga tgtcaaggcg    2820
ggtttcacca tcacaggatt gggctggcat ttcggacgtg tcgaaattaa agcctgttcc    2880
agtgggacca actttaaaat cagaaccaca tggtgacaat tttatagcag ttggtcttcg    2940
cggtgcactg tctgcttctg cagtgggatc acaactcgag tttgagctgg aataccgctg    3000
tatggagggg tttcagtttg cggacccctta tttaccgcca cgcagattat gtgccgatac    3060
ccgcaattat cttaagaatg gacgtcttcc ctaccgaata ccatcaaggg aatgggaatc    3120
ggacggcata ggtgaaccaa ccaaggtcaa gaaacaatct cgcttgaccg aggttgtaac    3180
tggtacagct ggaatcaatt taggtaaatc ttcccgggcc cattatgggt aacccttttga    3240 tgtttaaatt ttaattccgt tctcgccgga gatgagtacc ggtttgagtt taattcccag    3300
gtagcgcgag ccgtgagtca gcccagacaa gcgcagtagc cctacttgga gaggttctcc    3360
ttgagcgacc agaagctggc attgaatcga gtcacataat gctgagagta gagggatttg    3420
cattctattg tgaaagcaat aatttgagag ttaagcccat cacattgtgc actcggaata    3480
ttgtgcagcg cgaaaggtta gtaacattaa gttggcgaaa ggttagcgca gcaatgattg    3540
gtggtaacgc tggatcttat tgtggaagca atggatgaat atgaagttga aatcaggatc    3600
accacacccc cgcagcatag cggtaccgta ctgaatgtca caatccagtg atgattcgaa    3660
gcctataacg ggcggacgtg ttttaaatggt gttttatgtg atgttagtt cgccggaatg     3720 tgcagctccg gatatcgagt cgaagattca gtgaccagtg gagcaagcaa cataggtaac    3780
tatttcgtat gattttactc acaaaattgc actgggcagg agcttccaaa ggaaccttct    3840
gcttctcgta actgcacaca aactagattt cttattttcg gagagcatat caaaatggct    3900
tcaagttcaa gttcaagtaa tttgcaacct cgcaggaagt ttcaactccg cgacgaaatt    3960
cagagtgagg ggtggagaat acacctggaa tacacggaac gttatctata cgtgaaaggt    4020
gttgagttgc tcgaatatct tagggccctc gggagacgtc ttgcacaaca gcccgtgttt    4080
```

-continued

```
aattataagg ttcctaaggt cactccagtt tgccaagaac atatccataa gagagaagaa    4140
ggtggaacag attctactat agagtgtgta catgctgtaa aaactgcata cataaagctt    4200
aacctgacat ctgagggaat tcttttttgct ggatcagcaa tatgtaagaa ccattcagaa   4260
ctgtggaagt atactaagga ttttcaaaat tatatgcgcg aaaccttgta ccatcaactg    4320
atttcatcat ctaaacatga ccacacaaaa tggtattggg gaattttcca gaaaatgagt    4380
gttgatatga gtgatcccga gatttctagt atgggtgaga gcttcatgga aggtgcattg    4440
ttgagcagaa cccttcctga agaagtagca gaggattctc ttaaagaatc tgcacgcgaa    4500
gatttggctg aggaaacact tgacaagctg ctaactgaag ctgttgagcc atttgtggcg    4560
aacgccatat cacaaattaa cggattttta ttgtctgtca catcaatttt ggagtgtctt    4620
accacatcct tgaagatgat tctagtttta aagttatttt cctggatgtt ggagttttgg    4680
catacagttg atgctgaacc cacgagtttt ttcatggtgc tcttgggtgc tacctttgca    4740
tctgagttct ttaagctggc taaagattta tccatgggag ttgccgcttt tgagcgcctg    4800
tttgattatg gggttcgatt ctggaagttt atctcggagt ggatttctac acacatattt    4860
ggtcgtacac ctgaccgagt tacaatgcca cgtaaagtga tgaagttgat tttgaaaata    4920
aaatacttca atactgaggc tggattgaat gctgtaagaa tggctgagaa tgtaagagtt    4980
gaggctgaaa agctatttcc ggaatggaat gcattgctag cgcaatgccg tgacaatcct    5040
gaatatcgtc agatgtatca ggatttggag cggcagacac gcgcagttaa agaagttagc    5100
gactttgtca ctcgcttccg tgcagttttcc aatttccaac cgacgatgtt ccatgttcag    5160
ctagtgggac ggccaggaat tggtaagtct actttaatta agactatgac agctgatttg    5220
actcgatcgt tgtggccatc tgaaccaaaa ccatcattct acagtatgaa tatgaacttg    5280
gaattctttg atgggtatgc aggacagcgc ataatgattg cggatgacgt gtacaagatg    5340
aatgagccta agcatttaac agcaacgata ggccttataa cgaatacacc tgttatattg    5400
ccgatggcaa atctggctga taagggagtg cagcttacaa gtgaagtttt cttatcgacc    5460
acaaatactg cctatccatt gggcaaggat gttttgtgta tggaagcagt tcacaggaga    5520
cgtcatatgc tcgttgatgt aacatgtgac gagcgtgtaa tcgaggaggg tagtggacag    5580
ttttcagaag cactattccg acaatattat cctggacaag ataaatccaa gttcccacat    5640
cttaagttcg gccttatgaa gcctgtgcct aaagtgtttg gaggagctgc ggagaccgtt    5700
ctcgttggag aagatgagca gattgtttac aacgagtatg caaagttgct cagggatgca    5760
aatttcaaag tatccttggg tcataaggaa ttagatccaa cattttattt caatgaagag    5820
aatttgccgc aaggattttc gtatcctgcg cgtggttgga gttatgaaca gtttatgacc    5880
aattgcatgt ttagattccg ttcctttaga ggaatggagg aaagctatag tacggctgtc    5940
aagtatgcac acactgcaac ttgcctagct gagattgatg cattgctgga tcagaattct    6000
gactgtgatg gccctgaaat accaactgga gttggccgct tgatttgat taaaatgtat     6060 ggaaaagagt gtatgcatcc catgggaaca gatgatcctc tggggaagcg tattgcttct    6120
gatattgatg cccatagagc tactgcacct gagctagaac actttgatct tgatgcttgg    6180
gttgagaaga ccttggatgg atatattggt agaaatgaaa agcctactgg catcactctt    6240
gaggaagaaa gtacggcg tactactatc ttgcgcagaa gaagaaggc tattgttccc       6300 ccgcagttgc aagaagccct gaaagttcac cgacataatt tggattggta catcaggatc    6360
catgatcatc ccacaacgtg ggattccttgt gtgtttgaag gcaagaattt ggaggttgaa    6420
atgttgcaag cagtgatgat gcaggcatta tcacgtgttg taccaactag tctaatgtgt    6480
```

-continued

```
ggtggagatg gcatacgcaa catacaacca cctgagggct ttggatctag cgtctagaga    6540
aaatcaatgg ccgtcaccat gtgttgcaaa cctgtggata tagcttttg ttctgcaatt    6600 ttacagctga cgctttaccg gaacatacac ggaacggttt atgcggcact tttccacaaa    6660
tcactatcac gttaaatcaa ttgcatcact gttagtaata tagtgtatcg actaccatct    6720
tgaagagaaa aaggctcagt gtctccgtac cttgtcccag atgggggcca ttctgggttc    6780
ctgagaccca tcgcgactat tcccagcagt gagcggagtg aatttacggg gtagaacatt    6840
atccagttgt ccagcagtgt tgacgcaagt tcacctgtta ttgcacaagt atggatactt    6900
tataccaacc gaacttgtga agaatgtttc ccagagtatg gtgaatgcta gcttgtgaag    6960
atgagcatgt atttcaaatc acttgacagc gatagggatc cccgtttgcc tattatagag    7020
gcaaagtaaa tcctatcccg ataatcaaat attataaggg gcgtcttgac gaagcaatta    7080
cgggcactcg agaggatgga ggtatcccgt tcatatttga taagcgcgaa gatgaatttg    7140
gtgaagtgga ccatatagat gaagattccc tttcaaaggg tgaagttcca gaacttcgcc    7200
ctataaataa ggttttgggt gtaacgtgca tgaatgttta ctacattctt agtgctatgc    7260
accgtgcagc tgacggtact ggtccagaat ggtctgctct ttatcatcac gatgtttcca    7320
attgggatgg ttttcttttc ataaaagcaa taatgaacgt aaagaaggga ttctttgatg    7380
ttatgaattg tttcattcaa ggtattatat ctggcttccc cggaacggcg atagtatgta    7440
tttacctgat gcttgtcgca ttgcgcatgg tgtctgccat tttatatggt atcttgcatc    7500
tctttaatgg taaaacaata gtgacttctg ccacgaagtc cagtgagata ttcttaaaat    7560
ctagctggcg ccaacttctg gaagtagcct acgatctggt tcactgggtc ttccaaaatt    7620
acatggatgc actgtggatt agttttcagc tcaccgttaa tcagatttta agttacaaag    7680
attttgaaga cgactatttt ttgtagatag gttttttgga tgtcgtgacg ctagctggca    7740
aagtatcccc ttggcttaga ctccggttgg gcaatgcgtt tacctacgct tgttgtgtgt    7800
gtgttgacgt agaacctccg tttgtctgac acctatgtcg caccgatcta aatttcaatt    7860
tttcaaaatt taattcactg cggactccca taagtccgcc atgatttgtt ttgttttttct    7920 aaatttattt catttgttct attaaaaaaa aaaaaaaaa                          7959
```

<210> SEQ ID NO 2
<211> LENGTH: 23
<212> TYPE: DNA
<213> ORGANISM: Solenopsis invicta virus

<400> SEQUENCE: 2
atttgttttg gccacggtca aca                                            23

<210> SEQ ID NO 3
<211> LENGTH: 30
<212> TYPE: DNA
<213> ORGANISM: Solenopsis invicta virus

<400> SEQUENCE: 3
gatgatacaa agcattagcg taggtaaacg                                     30

<210> SEQ ID NO 4
<211> LENGTH: 31
<212> TYPE: DNA
<213> ORGANISM: Solenopsis invicta virus

<400> SEQUENCE: 4
cccaatcatt ccatttgtcc catgtgttgt c                                   31

```
<210> SEQ ID NO 5
<211> LENGTH: 38
<212> TYPE: DNA
<213> ORGANISM: Solenopsis invicta virus

<400> SEQUENCE: 5
ctgttatcaa gagtggctcc tcctccctaa atggattg                              38

<210> SEQ ID NO 6
<211> LENGTH: 39
<212> TYPE: DNA
<213> ORGANISM: Solenopsis invicta virus

<400> SEQUENCE: 6
cttcggaaaa tttcgttaaa atctgattaa cggtgagct                             39

<210> SEQ ID NO 7
<211> LENGTH: 28
<212> TYPE: DNA
<213> ORGANISM: Solenopsis invicta virus

<400> SEQUENCE: 7
agcgtaggta aacgcattgc ccaaccgg                                         28

<210> SEQ ID NO 8
<211> LENGTH: 19
<212> TYPE: DNA
<213> ORGANISM: Solenopsis invicta virus

<400> SEQUENCE: 8
tgcggaggtt ctacgtcaa                                                   19

<210> SEQ ID NO 9
<211> LENGTH: 23
<212> TYPE: DNA
<213> ORGANISM: Solenopsis invicta virus

<400> SEQUENCE: 9
tagatcggtg cgacataggt gtc                                              23

<210> SEQ ID NO 10
<211> LENGTH: 35
<212> TYPE: DNA
<213> ORGANISM: Solenopsis invicta virus

<400> SEQUENCE: 10
gaaagggaat cttcgaactt gtagtaccct tgaag                                 35

<210> SEQ ID NO 11
<211> LENGTH: 24
<212> TYPE: DNA
<213> ORGANISM: Solenopsis invicta virus

<400> SEQUENCE: 11
gtctttggtg gtgtgatttc atca                                             24

<210> SEQ ID NO 12
<211> LENGTH: 35
<212> TYPE: DNA
<213> ORGANISM: Solenopsis invicta virus

<400> SEQUENCE: 12
cagggactat atggagattg atgaatttgg tgaag                                 35
```

```
<210> SEQ ID NO 13
<211> LENGTH: 31
<212> TYPE: DNA
<213> ORGANISM: Solenopsis invicta virus

<400> SEQUENCE: 13
cggagacact gagcctttct ggactccata g                              31

<210> SEQ ID NO 14
<211> LENGTH: 21
<212> TYPE: DNA
<213> ORGANISM: Solenopsis invicta virus

<400> SEQUENCE: 14
tacacttggg tctcaggaac c                                         21

<210> SEQ ID NO 15
<211> LENGTH: 30
<212> TYPE: DNA
<213> ORGANISM: Solenopsis invicta virus

<400> SEQUENCE: 15
tgtatcgcgg aaattaccca acatcacaac                                30

<210> SEQ ID NO 16
<211> LENGTH: 25
<212> TYPE: DNA
<213> ORGANISM: Solenopsis invicta virus

<400> SEQUENCE: 16
ttccgcactg ctgggaatag tcgcg                                     25

<210> SEQ ID NO 17
<211> LENGTH: 20
<212> TYPE: DNA
<213> ORGANISM: Solenopsis invicta virus

<400> SEQUENCE: 17
ttgaggtcaa ggcgatcaac                                           20

<210> SEQ ID NO 18
<211> LENGTH: 33
<212> TYPE: DNA
<213> ORGANISM: Solenopsis invicta virus

<400> SEQUENCE: 18
cacttgtgca ataacaggtg atccacttct tcc                            33

<210> SEQ ID NO 19
<211> LENGTH: 23
<212> TYPE: DNA
<213> ORGANISM: Solenopsis invicta virus

<400> SEQUENCE: 19
gagaacagtg atgcaattga ttt                                       23

<210> SEQ ID NO 20
<211> LENGTH: 33
<212> TYPE: DNA
<213> ORGANISM: Solenopsis invicta virus

<400> SEQUENCE: 20
tcagtccatt tgagtagacc tttgcaacac atg                            33
```

```
<210> SEQ ID NO 21
<211> LENGTH: 16
<212> TYPE: DNA
<213> ORGANISM: Solenopsis invicta virus

<400> SEQUENCE: 21
ctgcggcaaa ttctct                                                      16

<210> SEQ ID NO 22
<211> LENGTH: 31
<212> TYPE: DNA
<213> ORGANISM: Solenopsis invicta virus

<400> SEQUENCE: 22
tgcatactcg ttgtaaacaa tctgctcatc t                                     31

<210> SEQ ID NO 23
<211> LENGTH: 23
<212> TYPE: DNA
<213> ORGANISM: Solenopsis invicta virus

<400> SEQUENCE: 23
taaagtagac ttaccaattc ctg                                              23

<210> SEQ ID NO 24
<211> LENGTH: 23
<212> TYPE: DNA
<213> ORGANISM: Solenopsis invicta virus

<400> SEQUENCE: 24
taaagtagac ttaccaattc ctg                                              23

<210> SEQ ID NO 25
<211> LENGTH: 32
<212> TYPE: DNA
<213> ORGANISM: Solenopsis invicta virus

<400> SEQUENCE: 25
tacatctgac gatattcagg attgtcacgg ca                                    32

<210> SEQ ID NO 26
<211> LENGTH: 32
<212> TYPE: DNA
<213> ORGANISM: Solenopsis invicta virus

<400> SEQUENCE: 26
tgccgtgaca atcctgaata tcgtcagatg ta                                    32

<210> SEQ ID NO 27
<211> LENGTH: 36
<212> TYPE: DNA
<213> ORGANISM: Solenopsis invicta virus

<400> SEQUENCE: 27
gacttgtcca aatgtccttg gacttcataa ccagct                                36

<210> SEQ ID NO 28
<211> LENGTH: 19
<212> TYPE: DNA
<213> ORGANISM: Solenopsis invicta virus

<400> SEQUENCE: 28
ttcctgagaa accttccat                                                   19
```

```
<210> SEQ ID NO 29
<211> LENGTH: 29
<212> TYPE: DNA
<213> ORGANISM: Solenopsis invicta virus

<400> SEQUENCE: 29
aaaggattcc ctcagatgtc aggttggaa                              29

<210> SEQ ID NO 30
<211> LENGTH: 32
<212> TYPE: DNA
<213> ORGANISM: Solenopsis invicta virus

<400> SEQUENCE: 30
tccagcgact cctcgaatga taagatgtag ac                          32

<210> SEQ ID NO 31
<211> LENGTH: 28
<212> TYPE: DNA
<213> ORGANISM: Solenopsis invicta virus

<400> SEQUENCE: 31
tggaagtttc aactccgcga cgaaatta                               28

<210> SEQ ID NO 32
<211> LENGTH: 28
<212> TYPE: DNA
<213> ORGANISM: Solenopsis invicta virus

<400> SEQUENCE: 32
taatttcgtc gcggagttga aacttcca                               28

<210> SEQ ID NO 33
<211> LENGTH: 28
<212> TYPE: DNA
<213> ORGANISM: Solenopsis invicta virus

<400> SEQUENCE: 33
ctttcgcact gcacaatatt ccgagtgc                               28

<210> SEQ ID NO 34
<211> LENGTH: 35
<212> TYPE: DNA
<213> ORGANISM: Solenopsis invicta virus

<400> SEQUENCE: 34
gatgctttat atgagtgatc ctgacgctgg attgc                       35

<210> SEQ ID NO 35
<211> LENGTH: 32
<212> TYPE: DNA
<213> ORGANISM: Solenopsis invicta virus

<400> SEQUENCE: 35
actgagtcac cagagaagtc atcgtgtggg tc                          32

<210> SEQ ID NO 36
<211> LENGTH: 36
<212> TYPE: DNA
<213> ORGANISM: Solenopsis invicta virus

<400> SEQUENCE: 36
gctctgctgt tcacgaataa gatctgcatt aagacc                      36
```

```
<210> SEQ ID NO 37
<211> LENGTH: 28
<212> TYPE: DNA
<213> ORGANISM: Solenopsis invicta virus

<400> SEQUENCE: 37
actgctactg ccagggactc aatttgcg                                      28

<210> SEQ ID NO 38
<211> LENGTH: 33
<212> TYPE: DNA
<213> ORGANISM: Solenopsis invicta virus

<400> SEQUENCE: 38
ttggtacagt gggaactttg cttcttctgg gat                                33

<210> SEQ ID NO 39
<211> LENGTH: 28
<212> TYPE: DNA
<213> ORGANISM: Solenopsis invicta virus

<400> SEQUENCE: 39
ggtgccatgc aataccgcat tcgtggtt                                      28

<210> SEQ ID NO 40
<211> LENGTH: 36
<212> TYPE: DNA
<213> ORGANISM: Solenopsis invicta virus

<400> SEQUENCE: 40
gaatggagac aggagcagta cacacaagat caactg                             36

<210> SEQ ID NO 41
<211> LENGTH: 37
<212> TYPE: DNA
<213> ORGANISM: Solenopsis invicta virus

<400> SEQUENCE: 41
gagaagatga gcagattgtt tacaacgagt atgcaaa                            37

<210> SEQ ID NO 42
<211> LENGTH: 31
<212> TYPE: DNA
<213> ORGANISM: Solenopsis invicta virus

<400> SEQUENCE: 42
cactccggtt ttatccacag tggtcgggtc t                                  31

<210> SEQ ID NO 43
<211> LENGTH: 52
<212> TYPE: PRT
<213> ORGANISM: Solenopsis invicta virus

<400> SEQUENCE: 43

Pro Lys Met Arg Pro Ile Thr Val Trp Leu Thr Gly Glu Ser Gly Ile
1               5                   10                  15

Gly Lys Thr Gln Gln Lys Ile Val Ile Tyr Asp Asp Ala Phe His Met
            20                  25                  30

Ala Ala Leu Gln Asp Lys Asn Met Tyr Ser Gln Ala Glu Val Leu Leu
        35                  40                  45

Tyr Thr Thr Asn
    50
```

<210> SEQ ID NO 44
<211> LENGTH: 53
<212> TYPE: PRT
<213> ORGANISM: Solenopsis invicta virus

<400> SEQUENCE: 44

Leu Arg Pro Pro Val Ser Leu Leu Leu Gly Gly Thr Gly Arg
1               5                   10                  15

Gly Lys Thr Thr Gln Leu Ile Thr Val Phe Asp Asp Phe Met His Met
            20                  25                  30

Ala Asn Leu Glu Asp Lys Asn Asn Thr Trp Phe Arg Ser Ser Val Ile
        35                  40                  45

Leu Ala Ser Ser Asn
    50

<210> SEQ ID NO 45
<211> LENGTH: 53
<212> TYPE: PRT
<213> ORGANISM: Solenopsis invicta virus

<400> SEQUENCE: 45

Pro Arg Thr Gln Pro Val Val Ile Trp Leu Phe Gly Glu Ser Gly Val
1               5                   10                  15

Gly Lys Ser Gly Gln Asn Val Val Ile Tyr Asp Asp Phe Gly His Met
            20                  25                  30

Ala His Leu Glu Asp Lys Arg Lys Thr Lys Phe Thr Ser Lys Ile Leu
        35                  40                  45

Leu Met Thr Ser Asn
    50

<210> SEQ ID NO 46
<211> LENGTH: 52
<212> TYPE: PRT
<213> ORGANISM: Solenopsis invicta virus

<400> SEQUENCE: 46

Val Arg Phe Glu Pro Phe Val Val Trp Ile Phe Gly Pro Arg Gly Val
1               5                   10                  15

Gly Lys Ser Thr Gln Pro Ile Val Leu Tyr Asp Asp Ile Gly Glu Lys
            20                  25                  30

Pro Arg Ile Glu Glu Lys Glu Ser Leu Met Thr Ser Val Ile Val Gly
        35                  40                  45

Ile Ala Ser Asn
    50

<210> SEQ ID NO 47
<211> LENGTH: 52
<212> TYPE: PRT
<213> ORGANISM: Solenopsis invicta virus

<400> SEQUENCE: 47

Val Arg Tyr Glu Pro Phe Val Ile Cys Ile Glu Gly Pro Ala Gly Ile
1               5                   10                  15

Gly Lys Ser Glu Gln Pro Val Val Tyr Asp Asp Trp Ala Glu Met
            20                  25                  30

Ala His Leu Glu Glu Lys Lys Ile Arg Gly Asn Pro Leu Ile Val Ile
        35                  40                  45

Leu Leu Cys Asn
    50

```
<210> SEQ ID NO 48
<211> LENGTH: 52
<212> TYPE: PRT
<213> ORGANISM: Solenopsis invicta virus

<400> SEQUENCE: 48

Phe Gln Pro Thr Met Phe His Val Gln Leu Val Gly Arg Pro Gly Ile
1               5                   10                  15

Gly Lys Ser Thr Gln Arg Ile Met Ile Ala Asp Asp Val Tyr Pro Met
            20                  25                  30

Ala Asn Leu Ala Asp Lys Gly Val Gln Leu Thr Ser Glu Val Phe Leu
        35                  40                  45

Ser Thr Thr Asn
    50

<210> SEQ ID NO 49
<211> LENGTH: 74
<212> TYPE: PRT
<213> ORGANISM: Solenopsis invicta virus

<400> SEQUENCE: 49

Leu Lys Asp Glu Arg Arg Pro Ile Glu Lys Val Asp Ala Gly Lys Thr
1               5                   10                  15

Arg Val Phe Ser Ala Gly Pro Gln His Phe Val Ala Phe Arg Lys
            20                  25                  30

Tyr Phe Leu Pro Phe Ala Ala Tyr Leu Met Asn Asn Arg Ile Asp Asn
        35                  40                  45

Glu Ile Ala Val Gly Thr Asn Val Tyr Ser Thr Asp Trp Glu Gly Asp
    50                  55                  60

Phe Gly Asn Phe Asp Gly Ser Leu Val Ala
65                  70

<210> SEQ ID NO 50
<211> LENGTH: 72
<212> TYPE: PRT
<213> ORGANISM: Solenopsis invicta virus

<400> SEQUENCE: 50

Leu Lys Asp Glu Arg Lys Ala Ile Glu Lys Ala His Lys Thr Arg Leu
1               5                   10                  15

Phe Ser Ala Ser Pro Leu Pro Tyr Leu Ile Leu Cys Arg Met Tyr Leu
            20                  25                  30

Gln Gly Gly Val Ser Arg Leu Arg Gly Lys Ile Val Asn Asn Ile
        35                  40                  45

Ala Val Gly Thr Asn Pro Tyr Ser Asp Asp Trp Thr Gly Asp Phe Ala
    50                  55                  60

Ser Tyr Asp Ser Ser Gln Glu Lys
65                  70

<210> SEQ ID NO 51
<211> LENGTH: 74
<212> TYPE: PRT
<213> ORGANISM: Solenopsis invicta virus

<400> SEQUENCE: 51

Leu Lys Asp Glu Arg Arg Pro Ile Glu Lys Val Asp Ala Leu Lys Thr
1               5                   10                  15

Arg Val Phe Ser Asn Gly Pro Met Asp Phe Asn Leu Ala Phe Arg Lys
            20                  25                  30
```

```
Tyr Phe Leu Gly Phe Ile Ala His Leu Met Glu Asn Arg Ile Asp Asn
            35                  40                  45

Glu Val Ala Ile Gly Thr Asn Val Tyr Ser Arg Asp Trp Thr Gly Asp
 50                  55                  60

Phe Ser Asn Phe Asp Gly Ser Leu Asn Ala
65                  70
```

<210> SEQ ID NO 52
<211> LENGTH: 75
<212> TYPE: PRT
<213> ORGANISM: Solenopsis invicta virus

<400> SEQUENCE: 52

```
Leu Lys Asp Glu Leu Arg Pro Ser Glu Lys Leu Arg Arg Phe Gly Gly
1               5                  10                  15

Thr Arg Val Phe Ser Val Pro Pro Leu Glu Leu Val Leu Asn Ser Arg
                20                  25                  30

Arg Phe Leu Leu Pro Phe Met Asp Ala Phe Gln Ser Phe Pro Ile Glu
            35                  40                  45

Ala His His Ala Ile Gly Leu Asn Pro Asn Ser Gly Asp Trp Arg Met
 50                  55                  60

Asp Tyr Lys Asn Tyr Ser Asp Ala Ile Pro Lys
65                  70                  75
```

<210> SEQ ID NO 53
<211> LENGTH: 75
<212> TYPE: PRT
<213> ORGANISM: Solenopsis invicta virus

<400> SEQUENCE: 53

```
Leu Lys Asp Glu Arg Lys Leu Pro Glu Lys Val Arg Lys Tyr Gly Gly
1               5                  10                  15

Thr Arg Val Phe Cys Asn Pro Pro Ile Asp Tyr Ile Val Ser Met Arg
                20                  25                  30

Gln Tyr Tyr Met His Phe Val Ala Ala Phe Met Glu Gln Arg Phe Lys
            35                  40                  45

Leu Met His Ala Val Gly Ile Asn Val Gln Ser Thr Glu Trp Thr Ile
 50                  55                  60

Asp Tyr Ser Asn Phe Gly Pro Gly Phe Asn Ala
65                  70                  75
```

<210> SEQ ID NO 54
<211> LENGTH: 80
<212> TYPE: PRT
<213> ORGANISM: Solenopsis invicta virus

<400> SEQUENCE: 54

```
Pro Lys Asp Glu Leu Arg Pro Ile Asn Lys Val Leu Gly Asp Glu Thr
1               5                  10                  15

Thr Pro Pro Lys Thr Arg Ser Val Thr Cys Met Asn Val Tyr Tyr Ile
                20                  25                  30

Leu Ala Trp Arg Arg Tyr Thr Met Arg Phe Trp Ser Ala Met His Arg
            35                  40                  45

Ala Ala Asp Gly Thr Ser Met Phe Gly Pro Gly Ile Asn Pro Glu Gly
 50                  55                  60

Pro Glu Trp Ser Phe Asp Val Ser Asn Trp Asp Gly Phe Leu Phe Ala
65                  70                  75                  80
```

<210> SEQ ID NO 55

```
<211> LENGTH: 67
<212> TYPE: PRT
<213> ORGANISM: Solenopsis invicta virus

<400> SEQUENCE: 55

Thr His Ser Gln Pro Ser Gly Asn Pro Phe Thr Val Ile Ile Asn Cys
1               5                   10                  15

Leu Tyr Asn Ser Met Ile Met Met Ile Ser Tyr Gly Asp Asp Asn Cys
                20                  25                  30

Leu Ser Leu Ser Glu Ile His Phe Leu Lys Lys Arg Phe Val Phe Ser
            35                  40                  45

His Gln Leu Gln Arg Thr Val Ala Pro Leu Gln Lys Asp Val Ile Tyr
        50                  55                  60

Glu Met Leu
65

<210> SEQ ID NO 56
<211> LENGTH: 67
<212> TYPE: PRT
<213> ORGANISM: Solenopsis invicta virus

<400> SEQUENCE: 56

Ser Lys Ser Leu Pro Ser Gly His Phe Leu Thr Ser Ile Ile Asn Ser
1               5                   10                  15

Ile Phe Val Asn Ile Ala Met Ile Val Thr Tyr Gly Asp Asp His Val
                20                  25                  30

Ile Lys Leu Glu Glu Val Thr Phe Ile Lys Arg Ser Phe Arg Tyr Val
            35                  40                  45

Lys Glu Leu Asp Arg Trp Leu Ala Pro Leu Asp Leu Asn Ser Ile Leu
        50                  55                  60

Asp Cys Met
65

<210> SEQ ID NO 57
<211> LENGTH: 67
<212> TYPE: PRT
<213> ORGANISM: Solenopsis invicta virus

<400> SEQUENCE: 57

Thr His Ser Gln Pro Ser Gly Asn Pro Ala Thr Thr Pro Leu Asn Cys
1               5                   10                  15

Leu Ile Asn Ser Ile Gly Leu Leu Ile Ser Tyr Gly Asp Asp Asn Val
                20                  25                  30

Ile Thr Leu Glu Glu Val Ser Phe Leu Lys Arg Gly Phe Ile Phe Asn
            35                  40                  45

Glu Glu Arg Asn Cys Tyr Asp Ala Pro Leu Asp Ile Asn Thr Ile Leu
        50                  55                  60

Glu Met Ile
65

<210> SEQ ID NO 58
<211> LENGTH: 68
<212> TYPE: PRT
<213> ORGANISM: Solenopsis invicta virus

<400> SEQUENCE: 58

Asn Asn Gly Val Leu Ala Gly His Pro Met Thr Ser Val Val Asn Ser
1               5                   10                  15

Val Val Asn Leu Ile Leu Met Ile Ile Val Met Gly Asp Asp Val Val
                20                  25                  30
```

Ile Ser Phe Asp Lys Phe Glu Phe Leu Ser Arg Gly Phe Ser Asp Cys
                35                  40                  45

Asp Ala Tyr Pro Asp Ile Thr Phe Ala Pro Val Lys Thr Ile Ala Leu
         50                  55                  60

Phe Asp Cys Pro
65

<210> SEQ ID NO 59
<211> LENGTH: 67
<212> TYPE: PRT
<213> ORGANISM: Solenopsis invicta virus

<400> SEQUENCE: 59

Lys Cys Gly Ser Pro Ser Gly Ala Pro Ile Thr Val Val Ile Asn Thr
1               5                   10                  15

Leu Val Asn Ile Leu Ile Leu Phe Cys Tyr Gly Asp Asp Leu Ile Met
                20                  25                  30

Thr Leu Leu Asn Ser Thr Phe Leu Lys His Gly Phe His Pro His Glu
                35                  40                  45

Val Tyr Pro His Leu Trp Gln Ser Ala Leu Ala Trp Ser Ser Ile Asn
         50                  55                  60

Asp Thr Thr
65

<210> SEQ ID NO 60
<211> LENGTH: 66
<212> TYPE: PRT
<213> ORGANISM: Solenopsis invicta virus

<400> SEQUENCE: 60

Ser Arg Gly Ile Ile Ser Gly Phe Pro Gly Thr Ala Glu Val Asn Thr
1               5                   10                  15

Leu Ala His Ile Leu Leu Ile Ala Ile Leu Tyr Gly Asp Asp Ile Leu
                20                  25                  30

Leu Pro Leu Ser Gln Cys Gln Phe Leu Lys Ser Ser Trp Arg Gln Leu
                35                  40                  45

Leu Pro Gly Tyr Tyr Ile Arg Val Leu Asp Leu Glu Val Ala Tyr Asp
         50                  55                  60

Leu Val
65

<210> SEQ ID NO 61
<211> LENGTH: 83
<212> TYPE: PRT
<213> ORGANISM: Solenopsis invicta virus

<400> SEQUENCE: 61

Lys Leu Lys Gly Phe Val Gly Leu Arg Ala Thr Leu Val Leu Lys Val
1               5                   10                  15

Gln Val Asn Ser Gln Pro Phe Gln Gln Gly Arg Leu Met Leu Gln Tyr
                20                  25                  30

Ile Pro Tyr Cys Pro Thr Thr Asp Leu Glu Leu Ser Val Gly Thr Glu
                35                  40                  45

Val Glu Met Arg Ile Pro Tyr Tyr Tyr Asn Leu Ile Thr Gly Gln Gly
         50                  55                  60

Ser Phe Gly Ser Ile Tyr Val Val Tyr Ser Gln Leu His Asp Gln
65                  70                  75                  80

Val Ser Gly

<210> SEQ ID NO 62
<211> LENGTH: 82
<212> TYPE: PRT
<213> ORGANISM: Solenopsis invicta virus

<400> SEQUENCE: 62

Lys Phe Asp Gly Phe Ser Ser Phe Ser Ala Thr Val Glu Phe Lys Leu
1               5                   10                  15

Gln Ile Asn Ser Gln Pro Phe Gln Ala Gly Leu Leu Ile Met Gly Ala
            20                  25                  30

Leu Pro Ser Ile Pro His Thr Leu Phe Asp Ile Ser Lys Thr Ser Glu
        35                  40                  45

Ile Thr Leu Ser Val Pro Tyr Gln Tyr Asn Leu Val Leu Glu Pro Ile
    50                  55                  60

Asn Trp Ser Asn Phe Phe Ile Lys Val Tyr Ser Pro Leu Val Ser Lys
65                  70                  75                  80

Gln Thr

<210> SEQ ID NO 63
<211> LENGTH: 83
<212> TYPE: PRT
<213> ORGANISM: Solenopsis invicta virus

<400> SEQUENCE: 63

Lys Ala Asn Asn His Gln Tyr Phe Lys Ala Asp Cys Ile Lys Leu Val
1               5                   10                  15

Leu Asn Thr Asn Pro Met Val Ala Gly Arg Phe Trp Leu Thr Tyr Ser
            20                  25                  30

Pro Tyr Tyr Pro Gly Ile Glu Met Asp Val Gln Ile Asn Asp Ser Ala
        35                  40                  45

Glu Met Val Ile Pro Phe Ala Tyr Asp Leu Asn Thr Pro Thr Pro Glu
    50                  55                  60

Asp Phe Val Thr Leu Ser Leu Phe Gly Ile Thr Asp Leu Leu Ala Lys
65                  70                  75                  80

Asn Gly Asn

<210> SEQ ID NO 64
<211> LENGTH: 83
<212> TYPE: PRT
<213> ORGANISM: Solenopsis invicta virus

<400> SEQUENCE: 64

Ala Leu Arg Pro Phe Thr Leu Met Lys Thr Asp Leu Glu Ile Thr Leu
1               5                   10                  15

Lys Ile Asn Ser Asn Gln Ala Gln Ala Gly Arg Tyr Val Leu Ala Ser
            20                  25                  30

Tyr Pro Cys Glu His Val Glu Val Asp Val Ser Thr Ser Ala Asp Ala
        35                  40                  45

Ile Leu Gln Ile Lys Tyr Thr Asn Glu Val Gly Glu Thr Thr Gly Glu
    50                  55                  60

Ser Phe Thr Thr Leu Thr Leu Thr Cys Leu Ser Pro Val Asn Val Val
65                  70                  75                  80

Ala Gly Ala

<210> SEQ ID NO 65
<211> LENGTH: 79
<212> TYPE: PRT

<213> ORGANISM: Solenopsis invicta virus

<400> SEQUENCE: 65

Pro Phe Glu Thr Tyr Val Tyr Gly Lys Tyr Glu Leu Glu Met Lys Phe
1               5                   10                  15

Val Ala Asn Gly Asn Lys Phe Gln Cys Gly Lys Val Ile Ile Ser Arg
            20                  25                  30

Pro His Ile Met Leu Asp Leu Ser Thr Asn Asn Glu Gly Val Leu Lys
        35                  40                  45

Ile Pro Phe Thr Ala Thr Ala Gly Ile Arg Pro Gly Lys Phe Ala Ser
    50                  55                  60

Ile Tyr Val Gln Val Leu Ser Pro Leu Gln Thr Gly Glu Gly Gly
65                  70                  75

<210> SEQ ID NO 66
<211> LENGTH: 84
<212> TYPE: PRT
<213> ORGANISM: Solenopsis invicta virus

<400> SEQUENCE: 66

Leu Arg Asn Leu Phe Gly Leu Lys Ser Trp Thr Leu Asn Phe Thr Phe
1               5                   10                  15

Gln Phe Arg Ser Asn Phe Gln Gln Val Gly Gln Leu Ile Ile Phe Tyr
            20                  25                  30

Thr Asn Met Leu Pro His Arg Lys Ile Pro Met Gly Glu Asp Gln Asp
        35                  40                  45

Val Asp Asp Val Ser Leu Lys Trp Val Tyr Asp Tyr Thr Ser Tyr Leu
    50                  55                  60

Tyr Asp Met Gly Thr Leu Arg Leu His Val Pro Phe Pro Met Glu Val
65                  70                  75                  80

Ala Thr Gly Val

<210> SEQ ID NO 67
<211> LENGTH: 257
<212> TYPE: PRT
<213> ORGANISM: Solenopsis invicta virus

<400> SEQUENCE: 67

Met Glu Pro Gln Glu Gln Gln Lys Asn Glu Val Ile Ser Arg Ala Lys
1               5                   10                  15

Glu Ile Asp Thr Gly Ala Val Pro Leu Pro Met Ser Asn Val Ile Leu
            20                  25                  30

Gly Leu Pro Lys Pro Asp Pro Thr Val Asp Lys Thr Gly Val Met
        35                  40                  45

Ser Arg Pro Trp Ser Phe Ala Asp Leu Val Ser Gln Lys Arg Ile Val
    50                  55                  60

Ala Asp Leu His Ile Asp Asn Thr Thr Asn Gly Lys Val Trp Glu Phe
65                  70                  75                  80

His Asn Thr Trp Met Asn Val Leu Asn Thr Ile Phe Lys Thr Thr Gly
                85                  90                  95

Ser Thr Ala Gly Glu Glu His Leu Arg Asn Leu Phe Gly Leu Lys Ser
            100                 105                 110

Trp Thr Leu Asn Phe Thr Phe Gln Phe Arg Ser Asn Phe Gln Gln Val
        115                 120                 125

Gly Gln Leu Ile Ile Phe Tyr Thr Asn Met Pro Arg Leu Leu Lys Asn
    130                 135                 140

Tyr His Ser Ala Thr Asp Val Thr Glu Asp Tyr Tyr Ser Ser Tyr Met

| | | | 145 | | | 150 | | | 155 | | | 160 |
|---|---|---|---|---|---|---|---|---|---|---|---|---|

Val Gln Thr Gln Leu Pro His Arg Lys Ile Pro Met Gly Glu Asp Gln
     165     170     175

Asp Val Asp Val Ser Leu Lys Trp Ile Ser Pro His Ala Ala Ala Phe
    180     185     190

Gly Ser Asp Met Tyr Ala Asp Gly Gln Thr Val Tyr Asp Tyr Thr Ser
   195     200     205

Tyr Leu Tyr Asp Met Gly Thr Leu Arg Leu His Val Pro Phe Pro Met
 210     215     220

Glu Val Ala Thr Gly Val Asp Ser Ala Met Thr Val Arg Val Trp Thr
225     230     235     240

Trp Leu Ser Asp Leu Ala Thr Gly Ala Tyr Lys Pro Tyr Asp Ser Val
    245     250     255

Leu

<210> SEQ ID NO 68
<211> LENGTH: 269
<212> TYPE: PRT
<213> ORGANISM: Solenopsis invicta virus

<400> SEQUENCE: 68

Met Gln Asp Lys Gln Leu Arg Leu Ile Met Ser Thr Gln Gln Met Leu
1     5     10     15

Ser Phe Asn Pro Pro Arg Leu Val Asn Val Pro Gln Gln Pro Pro Pro
    20     25     30

Gln Thr Val Ser Met Thr Leu Glu His Ser Gly Val Pro Val Asp Glu
   35     40     45

Pro Leu Leu Val Thr Asp Ile Pro Pro Asp Phe Gln Trp Met Ala Gln
 50     55     60

Leu Gln Arg Tyr His Thr Ser Phe Val Val Ser Lys Asn Lys Asn Pro
65     70     75     80

Lys Asp Pro Leu Trp Arg Asp Asn Val His Thr Met Val Glu Thr Ser
    85     90     95

Asp Gly Asp Pro Tyr Lys Ile Ile Pro Ser Trp Asn Leu Leu Pro Met
   100     105     110

Val Thr Ser Arg Trp Trp Asn Gly Val Ile Ser Tyr Lys Leu Ile Ala
 115     120     125

Ile Lys Pro Pro Arg Val Thr Gly Lys Leu Leu Ile Arg Tyr Ser Phe
130     135     140

Asp Pro His Asp Asp Phe Ser Gly Asp Ser Val Arg Arg Gly Ile Cys
145     150     155     160

Lys Glu Trp Asp Leu Gly Gln Ser Ser Glu Cys Glu Phe Asp Val Val
    165     170     175

Ala Thr Asn Thr Ile Arg Ala Arg Pro Thr Trp Leu Pro Leu Ile Arg
   180     185     190

Ser Gly Asn Val Thr Gly Ala Tyr Trp Leu Asp Gln Tyr Leu Pro Tyr
 195     200     205

Gln Thr His Tyr Gly Ser Leu Met Ile Glu Leu Ala Gln Arg Ile Gln
 210     215     220

Val Gly Ser Ile Phe Pro Asp Ser Ile Arg Ile Leu Val Phe Lys Cys
225     230     235     240

Phe Lys Asn Ala Glu Phe Tyr Leu Pro Thr Asp Ala Arg Gly Asp Ser
    245     250     255

Pro His Phe Leu Ala Thr Val Pro Ser Gly Arg Lys Ala
   260     265

```
<210> SEQ ID NO 69
<211> LENGTH: 265
<212> TYPE: PRT
<213> ORGANISM: Solenopsis invicta virus

<400> SEQUENCE: 69

Met Asn Ala Glu Glu Pro Ile Gln Ser Val Gly Ala Asn Gln Ile Val
1               5                   10                  15

Gly Thr Gln Gly Asp Pro Leu Gln Glu Gln Pro Gln Val Pro Thr Thr
                20                  25                  30

Ala Met Pro Arg Gln Met Ser Phe Ser Ser Leu Ile Tyr Gln Trp Gln
            35                  40                  45

Pro Met Gly Leu Arg Val Val Val Asn Leu Pro Phe Val Gly Asp Asp
        50                  55                  60

Lys Asp Phe Leu Phe Tyr Ile Arg Asn Gly Pro Phe Ile Pro Tyr Pro
65                  70                  75                  80

Cys Lys Tyr Arg Asp Asp Ser Ile Ser Gln Glu Pro Gly Val Ser Leu
                85                  90                  95

Tyr Pro Ala Trp Val Met Met Ile Arg His Ser Glu Ile Thr Met Pro
            100                 105                 110

Phe Asp Tyr Pro Val Ala Tyr Tyr Asp Gln Phe Ala Trp Met Ser Arg
            115                 120                 125

Arg Val Ser Pro Ser Gln Asp Trp Ala Gly Ile Ser Asp Val Ser Lys
        130                 135                 140

Leu Lys Pro Val Pro Val Gly Pro Thr Leu Lys Ser Glu Pro His Gly
145                 150                 155                 160

Asp Asn Phe Ile Ala Val Gly Leu Arg Gly Ala Leu Ser Ala Ser Ala
                165                 170                 175

Val Gly Ser Gln Leu Glu Phe Glu Leu Glu Tyr Arg Cys Met Glu Gly
            180                 185                 190

Phe Gln Phe Ala Asp Pro Tyr Leu Pro Pro Arg Arg Leu Cys Ala Asp
        195                 200                 205

Thr Arg Asn Tyr Leu Lys Asn Gly Arg Leu Pro Tyr Arg Ile Pro Ser
    210                 215                 220

Arg Glu Trp Glu Ser Asp Gly Ile Gly Glu Pro Thr Lys Val Lys Lys
225                 230                 235                 240

Gln Ser Arg Leu Thr Glu Val Val Thr Gly Thr Ala Gly Ile Asn Leu
                245                 250                 255

Gly Lys Ser Ser Arg Ala His Tyr Gly
                260                 265
```

SOLENOPSIS INVICTA VIRUS

This application claims the benefit of U.S. provisional Patent Application No. 60/927,114, filed May 1, 2007.

BACKGROUND OF THE INVENTION

1. Field of the Invention

This invention relates to biological methods and products useful for the control of *Solenopsis invicta*. More specifically, the present invention is directed to a novel *Solenopsis invicta* virus, nucleic acids encoding the novel virus, biocontrol compositions, and methods of using the virus and/or biocontrol compositions for control of fire ants.

2. Description of the Related Art

Red imported fire ant, *Solenopsis invicta* (Buren), was first detected in the United States near Mobile, Ala. in the late 1920s (Lolling, USDA Insect Pest Surv. Bull., Volume 9, 241, 1929). Since that time, it has spread to encompass more than 128 million hectares, primarily in the southeastern United States (Williams et al., Am. Entomol., Volume 47, 146-159, 2001). Fire ants are known to destroy young citrus trees, growing crops, and germinating seeds. This has an economic impact on agriculture in infested areas. Telephone companies spend substantial amounts of money each year treating their electrical equipment to prevent fire ant invasion because fire ants accumulate at electrical contacts and can short out electrical equipment. Farm equipment can also be damaged by large fire any mounds. Fire ants also present a danger to wildlife, such as ground nesting birds and animals. Furthermore, fire ants are known to excavate the soil from under roadways causing damage.

Fire ants also pose health care problems to millions of people stung each year a significant number of which require medical care. Fire ant stings are also blamed for human deaths. Consequently, there is much interest in controlling these troublesome pests.

This interest has resulted in much research and resources being expended through the years to develop reagents and methods for controlling fire ants. While many useful insecticide formulations have resulted from this research, the problems associated with fire ants still exist because the relief gained by insecticide use is only temporary. Once the insecticide pressure is relaxed, fire ant populations invariably repopulate the areas. This reinfestation ability is attributed to the high reproductive capabilities, the efficient foraging behavior, and the ecological adaptability of the ants. While effective for controlling ants in relatively small defined areas, insecticides can create other problems. For example, some insecticides, which are effective at controlling fire ants, can pose a significant threat to the environment, including birds and mammals.

Although considerable research effort has been brought to bear against the red imported fire ant, it remains the primary pest ant species in infested areas; initial eradication trials failed, yielding to the wide distribution of pesticide-based control products and a federally imposed quarantine to prevent further spread. Recently, much of the research effort has focused on elucidating basic life processes in an attempt to develop unique control measures, and fostering the development of self-sustaining methods of control, including biocontrol organisms and microbes (Williams et al., Am, Entomol., Volume 49, 150-163, 2003).

A dearth of natural enemies of the red imported fire ant have been found in the U.S. including a neogregarine (Pereira et al., J. Invertebr. Pathology, Volume 81, 45-48, 2002) and a fungus (Pereira et al., J. Invertebr. Pathology, Volume 84, 38-44, 2004).

U.S. Pat. No. 6,660,290 discloses a non-sporulating mycelial stage of an insect-specific parasitic fungi for control of pests with fire ants listed as one of many examples of insects controlled by the biopesticide.

U.S. Pat. Nos. 4,925,663; 5,683,689; 6,254,864; and 6,403,085 disclose a biopesticide effective against fire ants that includes the fungus *Beauveria bassiana*.

There remains a need for biocontrol and/or microbial control agents that eliminate or at least reduce the spread of fire ant colonies using novel pathogens. The present invention described below is directed to a novel *Solenopsis invicta* virus useful for the control of fire ants which are different from prior art pathogens and their uses.

SUMMARY OF THE INVENTION

It is therefore an object of the present invention to provide a novel *Solenopsis invicta* virus (SINV-2) for biocontrol of *Solenopsis invicta*.

A further object of present invention is to provide a nucleic acid sequence of SINV-2 for production of primers and biocontrol compositions.

A still further object of the present invention is to provide nucleic acid sequence SEQ ID NO: 1.

Another object of the present invention is to provide a biocontrol method for controlling fire ants that includes applying a SINV selected from the group consisting of SINV-2, SINV-1, SINV-1A, and mixtures thereof, to a carrier that is a fire ant food source to form a biocontrol composition which is scattered near a fire ant colony.

Another object of the present invention is to provide a biocontrol composition comprising SINV-2 and an acceptable carrier.

A further object of the present invention is to provide a biocontrol composition comprising a virus selected from the group consisting of SINV-2, SINV-1, SINV-1A and mixtures thereof.

Further objects and advantages of the present invention will become apparent from the following description.

BRIEF DESCRIPTION OF THE DRAWINGS

FIGS. 1A-C is a drawing showing a schematic diagram of the *Solenopsis invicta* virus-2 (SINV-2) genome with a 5'-3' orientation. Representation of the genome cloning strategy including expressed sequenced tags 18F8 and 1G9 (contig 246, accession number EH413675) indicated by a line without arrowheads, 3'RACE reaction (line with arrow to the right) and 15 successive 5RACE reactions (lines with arrows to the left) is shown in 1(A).

FIG. 1(B) shows open reading frames in the sense direction. Start and stop codons are represented by a vertical line and arrow, respectively. All three reading frames (RF1-3) are presented. Only ORFs comprised of at least 50 codons are presented. FIG. 1(C) shows conserved protein domains illustrated in-ORFs 1-4.

FIGS. 2A-B are photographs showing-characterization of SINV-2. FIG. 2(A) shows the sensitivity of SINV-2 RNA to single-strand—specific RNase A. Control (−) or RNase A-digested (+) nucleic acids prepared from SINV-2 infected *S. invicta* worker ants. RT-PCR and PCR were conducted with SINV-2-specific (p64/p65) or *S. invicta* transferrin-specific (p297/p316) oligonucleotide primers. FIG. 2(B) is an electron micrograph of a virus-like particle purified from SINV-2-infected *S. invicta* workers.

FIGS. 3A-3C are charts showing alignments of conserved regions of the putative helicase (3A) SEQ ID NOS: 43-48, RdRp (3B) SEQ ID NOS: 49-60, and ORF1 (3C) SEQ ID NOS: 61-66 of S1NV-2 with corresponding sequences from the cricket paralysis virus (CrPV), plautia stali (PSIV), SINV-1, and sacbrood virus (SbY). The numbers on the left indicate the starting amino acids of aligned sequences. Identical residues in at least four of the six virus sequences are shown in reverse. Sequence motifs shown for the helicase (hel A, hel B, and hel C) and RdRp (I-VIII) correspond to those identified and reviewed by Koonin and Dolja (1993). Asterisks indicate residues thought to be crucial to the activity of the protein.

FIGS. 6(A)-(K) includes the amino acid sequence of ORFs 1-4, SEQ ID NO: 68-71 and the complete genome of SINV-2 (SEQ ID NO: 1)

DETAILED DESCRIPTION OF THE INVENTION

Figure 4:
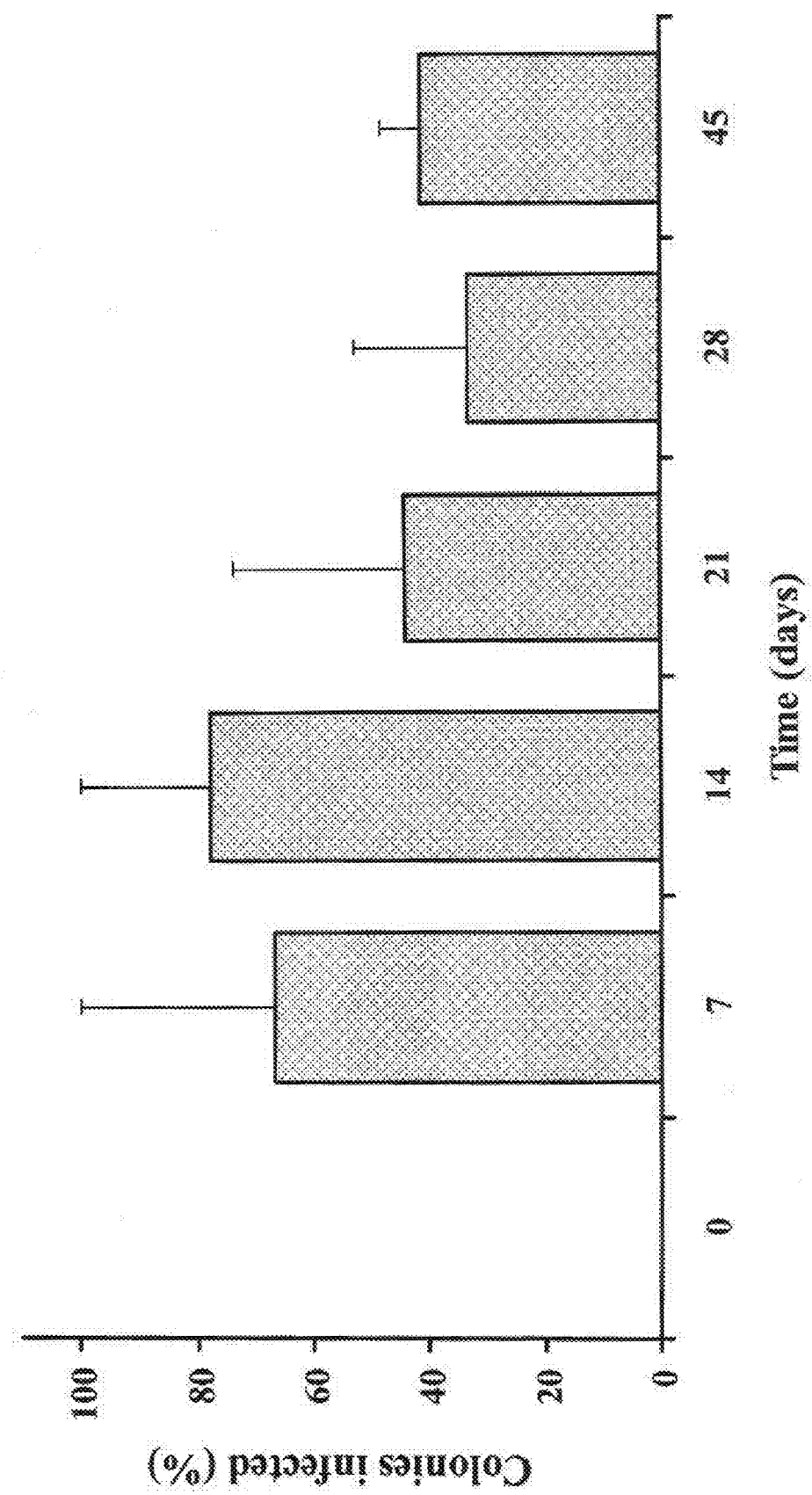
FIG. 4 is a graph showing transmission to uninfected *S. invicta* fragment colonies. Worker ants were sampled on the days specified and tested for the presence of SINV-2 by RT-PCR with oligonucleotide primers p64/p65.

Although viruses can be important biological control agents against insect populations (Lacey et al., Biol. Comtemp., Volume 21, 230-248, 2001), none have been shown to infect *Solenopsis invicta*. The only report present in the literature was the observation of "virus-like particles" in a *Solenopsis* species from Brazil (Avery et al., Brazil. Fla. Entomol., Volume 60, 17-20, 1977). *Solenopsis invicta* viruses (SINV) represent the first infection of the red imported fire ant by this group of organisms. In the laboratory SINV causes brood death of an entire colony and infection of healthy colonies (Valles et a., Virology,. Volume 328, 151-157, 2004; Valles et al., J. Invert. Path., Volume 88, 232-237, 2005; both references herein incorporated in their entirety).

U.S. Pat. No. 7,332,176, issued Feb. 19, 2008 (Valles et al) describes two viruses, SINV-1 and SINV1, useful for the control of *S. invicta* (herein incorporated by reference in its entirety).

The SINV-2 virus exhibits a monopartite, polycistronic, single-stranded RNA genome. The genome consensus sequence is approximately 11,303 nucleotides in length, excluding the poly(A) tail present on the 3' end. Analysis of the genome revealed 4 major open reading frames (ORFs; comprised of $\geq$100 codons) and 5 minor ORFs (comprised of approximately 50-99 codons) int the sense direction. No large ORFs were found in the inverse orientation suggesting that the SINV-2 genome was from a positive-strand RNA virus. Further evidence includes, abolished RT-PCR amplification by RNase treatment of SINV-2 nucleic acid template; and failure to amplify without first conducting cDNA synthesis. Blastp analysis indicated that ORF 4 contained conserved domains of an RNA-dependent RNA polymerase, helicase, and protease, characteristic of positive-strand RNA viruses. However, the protease domain and putative structural proteins, ORFs 1,2,and 3, were less well conserved. Phylogenetic analysis of the RdRp, helicase, and ORF1 indicate unique placement of SINV-2 exclusive from the Dicistroviridae, isflaviruses, Picomaviridae, and plant small RNA viruses.

SINV-2 represents the second virus discovered that infects the red imported fire ant, *S. invicta*. S1NV-2 is a unique virus with a genome that differs considerably from currently described positive-strand RNA viruses. Colonies infected with SINV-2 did not exhibit any discernable symptoms in the field or consistently when reared in the laboratory. However, some infected colonies exhibited brood die-off during laboratory rearing. These characteristics are consistent with other insect-infecting positive-strand RNA viruses, including SINV-1 (Valles et al, 2005, supra). They often persist as unapparent, asymptomatic infections that, under certain conditions, may induce replication within the host resulting in observable symptoms and often death (Christian and Scotti, 1998; Fernandez et al., 2001; Oldstone, Virology, Volume 344, 111-118, 2006).

Figures 2A, 2B:
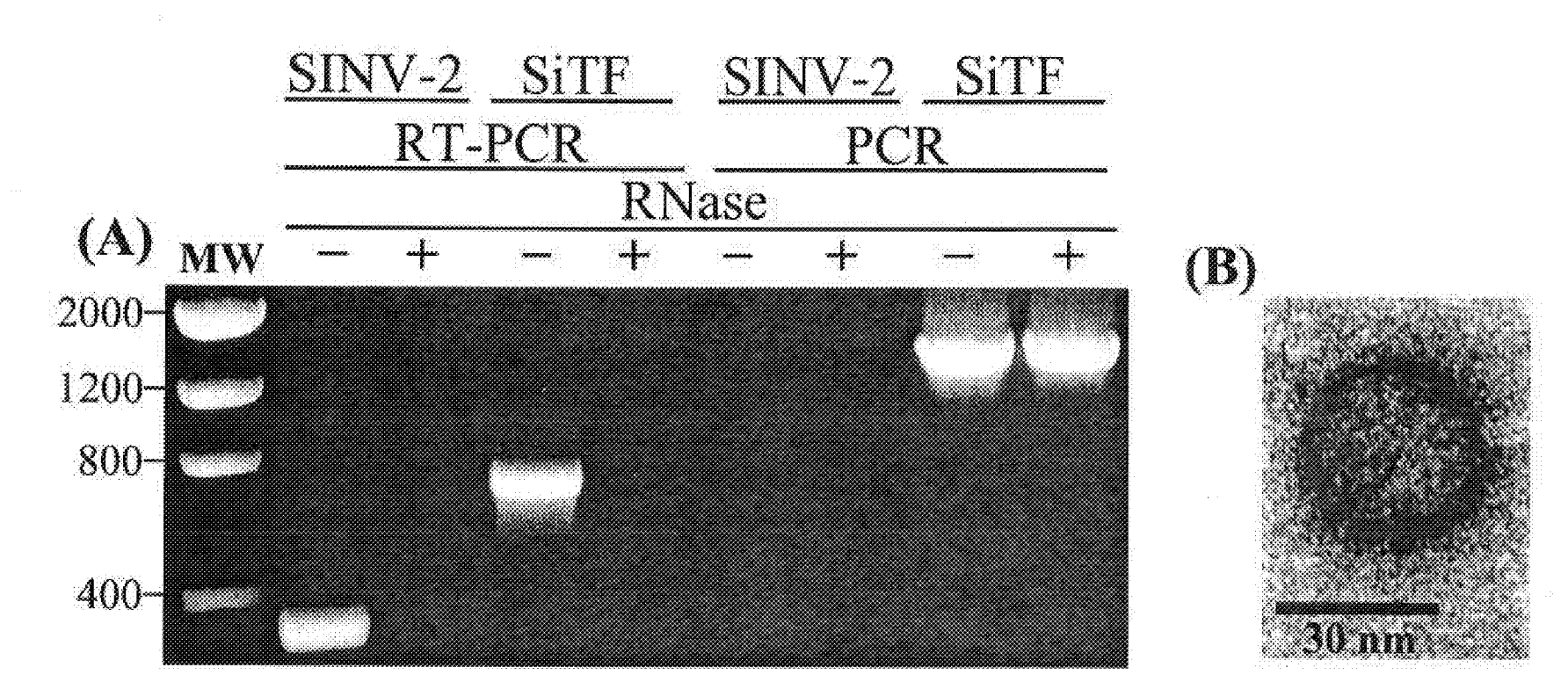

Isometric particles with a diameter of approximately 33 nm were found only in ants testing positive for SINV-2 by RT-PCR (FIG. 2B). This particle size was consistent with other positive-strand RNA viruses (Chen and Siede, Adv. Viral Res., (in press) 2007). Quantitative PCR (QPCR) revealed that the SINV-2 genome is most prevalent in the alimentary canals of worker ants. The alimentary tract is a common target of insect-infecting positive-strand RNA viruses (Gildow and D'Arcy, J. Invertebr. Pathol., Volume 55, 245-257,1990; Nakashima et al., J. Invertebr. Pathol., Volume 71, 151-158, 1998; van den Heuvel et al., J. Invertebr. Pathol., Volume 70, 169-176, 1997). SINV-1 also has been shown to exhibit alimentary canal tropism (Hashimoto and Valles, unpublished). These data are consistent with the inability to detect SINV-2 in fire ant pupae.

The SINV-2 genome structure was monopartite, polycistronic and RNA-based (FIGS. 1B and 2A). It appears that the non-structural proteins are found in the 3'-proximal ORF 4 and, structural, or capsid, proteins are encoded by ORFS 1 , 2, and 3. This structure is in direct contrast to SINV-1 which exhibits a dicistronic genome with non-structural proteins encoded by the 5' proximal ORF. Regions of the polyprotein encoded by SINV-2 ORF 4 exhibited significant homology to the RdRp and helicase of positive-strand RNA viruses (e.g. Dicistroviridae, Iflaviridae, and Picornaviridae). However, only a partial domain for a protease/peptidase was recognized near the amino end of the ORF 4 polyprotein (amino acid residues 330-410). A similarly unique genome structure was recently identified in the Nora virus that persistently infects *Drosophila melanogaster* (Habayeb et al., 2006). The Nora virus genome is also monopartite and polycistronic, possessing 4 major ORFs. However, RdRp and helicase were found in the second 5'-proximal ORF.

Figures 3A, 3B, 3C:
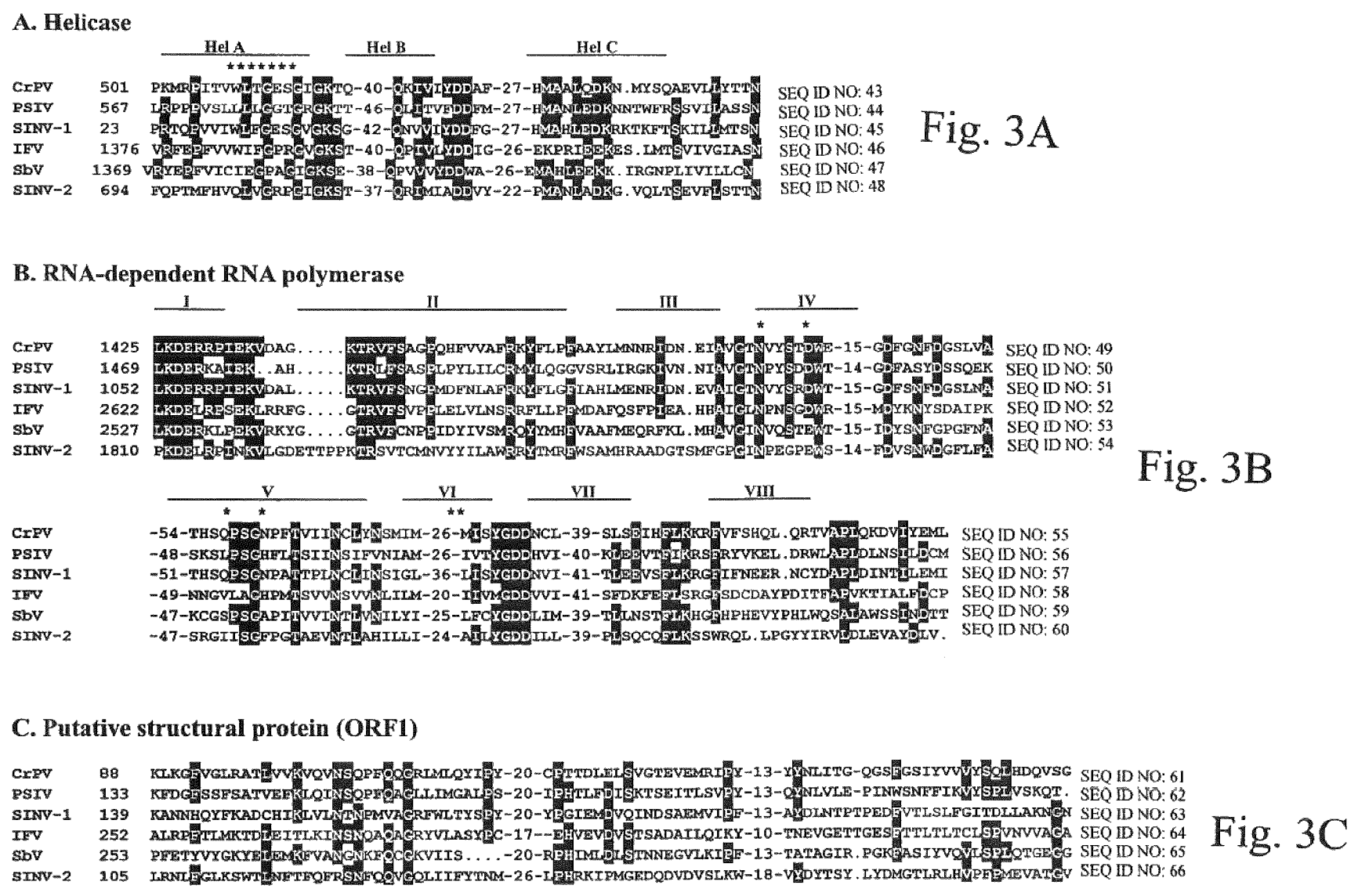

The SINV-2 polyprotein encoded by ORF 4 was aligned with non-structural regions of the cricket paralysis virus (CrPV), Plautia stali intestine virus (PSIV), *Solenopsis invicta* virus 1 (SINV-1), infectious flacherie virus (IFV), and sacbrood virus (SbV) using the Vector NTI alignment software with Clustal W algorithm (InforMax, Inc., Bethesda, Md.). The alignments revealed sequence motifs for an RdRp, helicase, and protease, characteristics of Picornaviridae, Dicistroviridae, and related positive-strand RNA viruses (Koonin and Dolja, Crit. Rev. Viochem. Molec. Biol., Volume 28, 375-430,1993) (FIG. 3). Amino acid positions 694 to 805 exhibited similarity to helicase. The consensus sequence for the RNA helicase, $Gx_4GK$ (Gorbalenya et al., FEBS Lett., Volume 262, 145-148, 1990), thought to be responsible for nucleotide binding, was found in the polyprotein of the SINV-2 ORF 4 at amino acids 706 to 712 (FIG. 3, motif Hel A). ORF 4 also encoded sequence with similarity to RdRp (amino acids 1,690 to 2,100; FIG. 3B). All positive-strand RNA viruses encode the RdRp (Koonin and Dolja, 1993, supra) and comparative analysis revealed that they possess 8 common sequence motifs (Koonin, J. Gen. Virol., Volume 72, 2197-2206, 1991). These core RdRp motifs were shown by site-directed mutagenesis to be crucial to the activity of the enzyme (Sankar and Porter, J. Biol. Chem., Volume 267, 10168-10176, 1992). All eight of these motifs were present in SINV-2 ORF 4 (FIG. 3B). Furthermore, the sequence motifs IV, V, and VI were reported to be unequivocally conserved throughout this class of viruses, exhibiting 6 invariant amino acid residuces (Koonin and Dolja, 1993, supra). SINV-2 ORF 4 possessed all 6 of these characteristic residues, $D^{1893}$, $D^{1898}$ (motif IV), $G^{1957}$, $T^{1961}$ (motif V), and $D^{2003}$, $D^{2004}$ (motif VI). Thus these data strongly support the conclusion that SINV-2 possesses an RdRp typically found in positive-strand RNA viruses.

Blastp analysis of ORF 4 also indicated that the region contained by amino acids 330 and 410 was consistent with a protease domain. However, only a partial domain was indicated. Furthermore, amino acids thought to form the catalytic triad of the protease (H,E,C) and the consensus GxCG sequence motif of positive-strand RNA viruses were absent in this region and across the entrie ORF (Koonin and Dolja, 1993, supra; Ryan and Flint, J. Gen. Virol., Volume 78, 699-723, 1997). Nor was this sequence motif found in ORFs 1,2, or 3. Habayeb et al (2006, supra) recently reported a similarly poorly conserved protease domain region in the Nora virus.

In contrast to Dicistroviridae (monopartite/dicistronic), iflaviruses, and Picornaviridae (monpartite/monocistronic), the SINV-2 genome appears to be unique with a monopartite poly(tetra)-cistronic genome organization. The largest ORF (4) contained domains consistent with the RdRp, helicase, and protease/peptidase of positive-strand RNA viruses. The remaining ORFs (1,2, and 3) putatively encode structural or capsid proteins. The SINV-2-genome organization is similar to that of the Nora virus which also encodes 4 major ORFs in a monopartite genome (Habayeb et al., J. Gen. Virol., Volume 87, 3045-3051, 2006). However, the positional organization of the ORFs is different between the Nora virus and SINV-2.

The present invention provides nucleic acids encoding for SINV-2 as set forth in SEQ ID NO: 1 (FIGS. 6A-6K). The invention also provides nucleic acid sequences (SEQ ID NO: 2-20) capable of selectively hybridizing DNA, RNA, and cDNA sequences which can be derived from SEQ ID NO: 1. To isolate SINV-2, RNA from fire ants, collected from a fire ant mound, was extracted from about 20-50 workers using TRIZOL reagent according to the manufacturer's directions (Invitrogen, Carlsbad, Calif.).

With the primers of the present invention, one of ordinary skill in the art could readily identify SINV viruses of the present invention.

For purposes of the present invention, the term "fire ant" and "*Solenopsis invicta*" are used interchangeably to describe the common red fire ant, originating in South America, but now commonly found in the United States, and Puerto Rico. The term fire ant also is used to describe black fire ants and other hybrid fire ants or other ants that are infected by the viruses of the present invention.

For purposes of the present invention, the term "isolated" is defined as separated from other viruses found in naturally occurring organisms.

For purposes of the present invention, the term "composition" is used to describe a composition which contains the virus of the presently claimed invention, optionally a carrier and optionally a pesticide. The carrier component can be a liquid or a solid material and is an inert, non-repellent carrier for delivering the composition to a desired site. Liquids suitable as carriers include water, and any liquid which will not affect the viability of the viruses of the present invention. Solid carriers can be anything which the fire ant will feed on. Non-limiting examples of solid carriers of the present invention include materials such as corn cob grits, extruded corn pellets, boiled egg yolks, and frozen insects such as crickets.

Optional toxicants include Chlorfenapyr, Imidacloprid, Fipronil, Hydramethylnon, Sulfluramid, Hexaflumuron, Pyriproxyfen, methoprene, lufenuron, dimilin, Chlorpyrifos, and their active derivatives, Neem, azadiractin, boric acid based, etc. The toxicant acts as a stressor which may be required to initiate viral replication which in turn results in brood death in the fire ant colony.

The term "effective amount" or "amount effective for" as used herein means that minimum amount of a virus composition needed to at least reduce, or substantially eradicate fire ants in a fire ant colony when compared to the same colony or other colony which is untreated. The precise amount needed will vary in accordance with the particular virus composition used; the colony to be treated; the environment in which the colony is located. The exact amount of virus composition needed can easily be determined by one having ordinary skill in the art given the teachings of the present specification. The examples herein show typical concentrations which will be needed to at least reduce the number of fire ants in a colony.

In the present method of using the viruses of the present invention, to reduce or eradicate a population of fire ants, the present compositions are delivered to the fire ants by spreading the composition at or near the fire ant colonies. The amount of composition used is an effective amount for producing the intended result, whether to reduce or eradicate the population of fire ants. The composition is prepared by homogenizing approximately 300 workers from a SINV infected colony in an equal volume of water and placing the resulting homogenate on a carrier.

The following examples are intended only to further illustrate the invention and are not intended to limit the scope of the invention as defined by the claims.

EXAMPLE 1

A one-step reverse transcriptase polymerase chain reaction (RT-PCR) was used to identify SINV-2-infected *S. invicta* ants. A 20 ml scintillation vial was plunged into a fire ant mound in the field for several minutes to collect a sample of the worker caste. The ants were returned to the laboratory and RNA was extracted from about 10-20 ants using TRIZOL reagent according to the manufacturer's directions (Invitrogen, Carlsbad, Calif.). cDNA was synthesized and subsequently amplified using the One-Step RT-PCR kit (Invitrogen) with oligonucleotide primers p64-SEQ ID NO: 2 and SEQ ID NO: 3 (Table 1). Samples were considered positive for the virus when a visible amplicon (about 319 nucleotides) was present after separation on about a 1.2% agarose gel stained with ethidium bromide. RT-PCR was conducted in a PTC 100 thermal cycler (MJ Research, Waltham, Mass.) Under the following optimized temperature regime:

1 cycle at about 45° C. for about 30 minutes;
1 cycle at about 94° C for about 2 minutes;
35 cycles at about 94° C. for about 15 seconds;
1 cycle at about 56° C. for about 15 seconds;
1 cycle at about 68° C. for about 30 seconds; and
a final elongation step of about 68° C. for about 5 minutes.

SINV-2 was purified for electron microscopy by the method described by Ghosh et al. (J. Gen. Virol., Volume 80, 1541-1549, 1999). Briefly, approximately 200 worker ants were homogenized in about 5 ml of NT buffer (Tris-HCl, pH about 7.4, approximately 10 mM NaCl) using a Potter-Elvehjem Teflon pestle and glass mortar. The mixture was clarified by centrifugation at about 1000 X g for about 10 minutes in an L8-70M ultracentrifuge (Beckman, Palo Alto, Calif.). The supernatant was extracted with an equal volume of 1,1,2-trichlortrifluoroethane before the aqueous phase was layered onto a discontinuous CsCl gradient (about 1.2 and about 1.5 g/ml) which was centrifuged at about 270,000 X g for about 1 hour in an SW60 rotor. A whitish band visible near the interface was removed by suction and desalted. The sample was negatively stained with about 2% phosphotungstic acid, about pH 7, and examined with a Hitachi H-600 transmission electron microscope (Hitachi, Pleasanton, Calif.) on a formvar film coated grid. Uninfected worker ants were prepared and examined in the same manner and served as controls.

A contiguous fragment (approximately 634 nucleotides) was assembled from ESTs 18F8 and 1G9 (contig c246, accession number EH413675) and used as the primary sequence from which oligonucleotide primers were designed and rapid amplification of 5' and 3' cDNA end PCR, RACE (3'and 5') reactions were conducted (FIG. 1A). From this fragment, a series of rapid amplification of 5' cDNA end PCR, 5'RACE reactions were conducted to obtain the upstream sequence of the SINV-2 genome using the rapid amplification of 3' cDNA end PCR, 5' RACE system (Invitrogen) and primer walking. Briefly, cDNA was synthesized with a gene-specific oligonucleotide primer (GSP) from total RNA, the RNA template was degraded with RNase H, and the cDNA purified. The 3' end of the cDNA was polycytidylated with terminal deoxynucleotidyl transferase and dCTP. The tailed cDNA was then amplified with a nested, upstream GSP and an abridged anchor primer (AAP; Table 1).

Fifteen successive rapid amplification of 5' cDNA end PCR, 5' RACE reactions were conducted to obtain the entire SINV-2 genome. Anticipating the potential need to remove the VPg often covalently attached to the insect picorna-like viruses (Christian and Scotti, In: "The insect viruses, 301-336, Plenum Publishing Corporation, N.Y., 1998), approximately 50 micrograms of total RNA prepared from SINV-2-infected ants was digested with proteinase K., approximately 600 micrograms/ml, for about 1 hour at approximately 37 degrees C. The digested RNA was purified by acidic phenol: chloroform:isoamyl alcohol extraction. cDNA sysnthesis was conducted for about 50 minutes at about 45 degrees C. with approximately 2.5 micrograms of total RNA and a GSP for the 15 reactions (FIG. 2A). After cDNA synthesis, PCR was conducted with AAP and arrested GSP. Gel purified amplicons were ligated into an expression vector, the pCR4-TOPO Vector, transformed into chemical competent *E. Coli* cells TOP10 competent cells (Invitrogen) and sequenced.

A single a rapid amplification of 3' RACE reaction was conducted with a GeneRacer kit (Invitrogen). cDNA was synthesized from total RNA, approximately 1 microgram, purified from SINV-2-infected workers using the GeneRacer Oligo dT primer. The cDNA was amplified by PCR with oligonucleotide primer p64 and the GeneRacer 3' primer. Amplicons were cloned and sequenced as described for a rapid amplification of 5' cDNA end PCR, 5' RACE.

Experiments were conducted to confirm the RNA characteristics of the SINV-2 genome. Nucleic acids purified from SINV-2-positive ants were divided into two aliquots of approximately 2 micrograms each. One aliquot was treated with approximately 33 micrograms (1 microliter) of RNaseA (Sigma) at about 37 degrees C. for about 1 hour in Tris-HCl, pH approximately 8.0. RNase-treated and -untreated samples were then evaluated by PCR and RT-PCR using oligonucleotide primers specific to SINV-2, p64 and p65, and to the *S. invicta* transferrin gene, p297 and p316, as an internal control (Valles and Pereira, Gene, Volume 358, 60-66, 2005).

The SINV-2 genome was constructed by compiling sequences from 15 successive 5' RACE reactions, one 3' RACE reaction, and EST c246 (EH413674) from the fire ant expression library (FIG. 1A). Subsequent RT-PCR amplification with overlapping oligonucleotide primers provided at least 5-fold coverage of the genome. The SINV-2 genome consensus sequence (Accession number EF428566) was 11,303 nucleotides in length, excluding the poly(A) tail present at the 3' end. The genome sequence was A/U rich (approximately 27.9% A, 28.9% U, 20.1% C, 23.1% G). Analysis of the genome revealed 4 major ORFs comprised of 100 codons) and 5 minor ORFs comprised of approximately 50-99 codons in the sense orientation (FIG. 1B). Among the major ORFs, ORF3 was in the first reading frame, ORFs 1 and 2 were in the second reading frame, and ORF 4 was in the third reading frame. ORFs 2 and 3 overlap a stop and start codon, respectively. ORF 1 was followed directly by 2 additional minor ORFs. ORFs 1 through 4 encoded predicted proteins of 29, 413; 31, 160; 43, 224; and 246,845 Da. No large ORFs were found in the reverse orientation suggesting that the SINV-2 genome was positive sense. FIG. 2A shows that RNase treatment of nucleic acid preparations from SINV-2-infected *S. invicta* failed to yield an amplicon by RT-PCR analysis. PCR also failed to yield an amplicon with oligonucleotide primers specific for SINV-2 indicating absence of a DNA stage or integration. The *S. invicta* transferrin (SiTF) gene, an internal control, produced an amplicon by PCR in both RNase A-treated and -untreated samples.

Blastp analysis (Altschul et al, Nucleic Acid Res., Volume 25, 3389-3402, 1997) of SINV-2 ORF 4 revealed significant (expectation score $\leq 10^5$) homology with RdRp and helicase conserved domains from positive-strand RNA viruses (FIGS. 1C and 3). No significant homology was indicated after blastp analysis of ORFs 1, 2 and 3 of the SINV-2 genome. However, capsid proteins of positive-strand RNA viruses were indicated (Expectation scores greater than 1).

Electron microscopic examination of negatively stained samples from SINV-2-infected fire ants revealed particles that were consistent with Picomaciridae, Dicistroviridae, and related positive-strand RNA viruses (FIG. 2B). Isometric particles with a diameter of approximately 33 nm were observed exclusively in preparations from SINV-2-infected fire ants; no corresponding particles were observed in samples prepared from uninfected fire ants.

TABLE 1

Oligonucleotide primers.

| Oligonucleotide Designation | Reaction | Oligonucleotide (5'→3') | Genome Position | Orientation |
|---|---|---|---|---|
| P64 | 3' Race/Ant infection | ATTTGTTTTGGCCACGGTCAACA SEQ ID NO: 2 | 10758-10780 | → |
| P65 | Ant Infection | GATGATACAAAGCATTAGCGTAGGTAAACG SEQ ID NO: 3 | 11047-11076 | ← |
| p297 | Transferrin | CCCAATCATTCCATTTGTCCCATGTGTTGTC SEQ ID NO: 4 | NA | ← |
| p316 | Transferrin | CTGTTATCAAGAGTGGCTCCTCCTCCCTAAATGGATTG SEQ ID NO: 5 | NA | → |
| p479 | Genome | CTTCGGAAAATTTCGTTAAAATCTGATTAACGGTGAGCT SEQ ID NO: 6 | 10798-10836 | ← |
| p480 | 5' RACE/Coverage | AGCGTAGGTAAACGCATTGCCCAACCGG SEQ ID NO: 7 | 11033-11060 | ← |
| p482 | cDNA synthesis | TGCGGAGGTTCTACGTCAA SEQ ID NO: 8 | 11104-11122 | ← |
| P483 | cDNA synthesis | TAGATCGGTGCGACATAGGTGTC SEQ ID NO: 9 | 11158-11180 | ← |
| P500 | 5' RACE/Coverage | GAAAGGGAATCTTCGAACTTGTAGTACCCTTGAAG SEQ ID NO: 10 | 9810-9844 | ← |
| p502 | cDNA synthesis | GTCTTTGGTGGTGTGATTTCATCA SEQ ID NO: 11 | 9920-9943 | ← |
| p504 | Coverage | CAGGGACTATATGGAGATTGATGAATTTGGTGAAG SEQ ID NO: 12 | 9752-9786 | → |
| p511 | QPCR | CGGAGACACTGAGCCTTTCTGGACTCCATAG SEQ ID NO: 13 | 8677-8707 | ← |
| p514 | QPCR (RT) | TACACTTGGGTCTCAGGAACC SEQ ID NO: 14 | 8816-8836 | ← |
| p515 | Coverage/QPCR | TGTATCGCGGAAATTACCCAACATCACAAC SEQ ID NO: 15 | 8585-8613 | → |
| p525 | 5' RACE | TTCCGCACTGCTGGGAATAGTCGCG SEQ ID NO: 16 | 8872-8896 | ← |
| p527 | cDNA synthesis | TTGAGGTCAAGGCGATCAAC SEQ ID NO: 17 | 9018-9037 | ← |
| p541 | Coverage | CACTTGTGCAATAACAGGTGATCCACTTCTTCC SEQ ID NO: 18 | 9099-9131 | ← |
| p542 | cDNA synthesis | GAGAACAGTGATGCAATTGATTT SEQ ID NO: 19 | 8514-8536 | ← |
| p545 | 5' RACE | TCAGTCCATTTGAGTAGACCTTTGCAACACATG SEQ ID NO: 20 | 8158-8190 | ← |
| p546 | cDNA synthesis | CTGCGGCAAATTCTCT SEQ ID NO: 21 | 7217-7232 | ← |
| p548 | 5' RACE/Coverage | TGCATACTCGTTGTAAACAATCTGCTCATCT SEQ ID NO: 22 | 7112-7142 | ← |
| p549 | Coverage | ACGGTCTCCGCAGCTCCTCCAAACACT SEQ ID NO: 23 | 7073-7099 | ← |
| p551 | cDNZ synthesis | TAAAGTAGACTTACCAATTCCTG SEQ ID NO: 24 | 6574-6596 | ← |
| p554 | 5' RACE | TACATCTGACGATATTCAGGATTGTCACGGCA SEQ ID NO: 25 | 6426-6457 | ← |
| p555 | Coverage | TGCCGTGACAATCCTGAATATCGTCAGATGTA SEQ ID NO: 26 | 6426-6457 | → |
| p560 | 5' RACE/Coverage | GACTTGTCCAAATGTCCTTGGACTTCATAACCAGCT SEQ ID NO: 27 | 5656-5690 | ← |
| p563 | cDNA synthesis | TTCCTGAGAAACCTTCCAT SEQ ID NO: 28 | 5787-5805 | ← |

TABLE 1-continued

Oligonucleotide primers.

| Oligonucleotide Designation | Reaction | Oligonucleotide (5'→3') | Genome Position | Orientation |
|---|---|---|---|---|
| p573 | 5' RACE/Coverage | AAAGGATTCCCTCAGATGTCAGGTTGGAA SEQ ID NO: 29 | 5027-5055 | ← |
| p574 | cDNA synthesis | TCCAGCGACTCCTCGAATGATAAGATGTAGAC SEQ ID NO: 30 | 5062-5093 | ← |
| p579 | Coverage | TGGAAGTTTCAACTCCGCGACGAAATTA SEQ ID NO: 31 | 4494-4521 | → |
| p580 | 5' RACE | TAATTTCGTCGCGGAGTTGAAACTTCCA SEQ ID NO: 32 | 4494-4521 | ← |
| p588 | 5' RACE | CTTTCGCACTGCACAATATTCCGAGTGC SEQ ID NO: 33 | 4029-4056 | ← |
| p599 | 5' RACE/Coverage | GATGCTTTATATGAGTGATCCTGACGCTGGATTGC SEQ ID NO: 34 | 3232-3266 | ← |
| p602 | 5' RACE | ACTGAGTCACCAGAGAAGTCATCGTGTGGGTC SEQ ID NO: 36 | 2261-2292 | ← |
| p610 | 5' RACE | GCTCTGCTGTTCACGAATAAGATCTGCATTAAGACC SEQ ID NO: 37 | 1603-1638 | ← |
| p615 | 5' RACE | ACTGCTACTGCCAGGGACTCAATTTGCG SEQ ID NO: 38 | 1167-1194 | ← |
| p617 | Genome/Coverage | TTGGTACAGTGGGAACTTTGCTTCTTCTGGGAT SEQ ID NO: 39 | 1113-1145 | → |
| p619 | Coverage | GGTGCCATGCAATACCGCATTCGTGGTT SEQ ID NO: 40 | 3109-3125 | → |
| p621 | Coverage | GAATGGAGACAGGAGCAGTACACACAAGATCAACTG SEQ ID NO: 41 | 5118-5153 | → |
| p623 | Coverage | GAGAAGATGAGCAGATTGTTTACAACGAGTATGCAAA SEQ ID NO: 42 | 7108-7144 | → |
| p632 | 5' RACE | CACTCCGGTTTTATCCACAGTGGTCGGGTCT SEQ ID NO: 43 | 415-445 | ← |

EXAMPLE 2

A field survey was conducted to examine the extent of the SINV-2 infection among *S. invicta* nests from locations in and around Gainesville, Fla. Samples of workers were retrieved from the field and treated as described above in Example 1. SINV-2-specific oligonucleotide primers p64 SEQ ID NO: 2 and p65 SEQ ID NO: 3 were used in an RT-PCR reaction to determine the presence of infection. In an effort to determine possible ant social form-specificity of SINV-2, each nest that tested positive for SINV-2 was also genotyped at the Gp-9 locus to determine the social form of the nest (Valles and Porter Insectes Soc., Volume 50, 199-200, 2003).

Experiments were conducted to determine if the virus was present in different developmental stages. Samples of queens workers, early instars ($1^{st}$ and $2^{nd}$), late instars ($3^{rd}$ an $4^{th}$), eggs, and pupae were sampled directly from the field from SINV-2-positive colonies. All samples were analyzed for infection by the RT-PCR method.

Among 259 *S. invicta* nests samples within a one year period, 14 (5.4%) were found to be infected with SINV-2 (Table 2) by RT-PCR. No social form specificity was evident as monogyne (approximately 2.3%) and polygyne (approximately 3.1%) nests were found to harbor the virus (Table 2). The infection was detected in eggs, early $1^{st}$-$2^{nd}$) and late ($3^{rd}$-$4^{th}$) instars, workers, and queens. However, SINV-2 was not detected in pupae taken from five SINV-2-infected colonies.

TABLE 2

Prevalence of SINV-2 infection and corresponding Gp-9 genotype of *Solenopsis invicta* workers from infected nests.

| Collection | | Nests Sampled | Nests Infected with SINV-2 | SINV-2-infected nests with Gp-9 genotype | |
|---|---|---|---|---|---|
| Date | Location | | | BB | Bb |
| January | Gainesville, FL | 64 | 1 | | 1 |
| April | Gainesville, FL | 10 | 1 | | 1 |
| May | Gainesville, FL | 25 | 0 | | |
| August | Lake City, FL | 20 | 0 | | |
| August | Micanopy, FL | 15 | 0 | | |
| August | Gainesville, FL | 50 | 3 | 1 | 2 |
| October | Gainesville, FL | 25 | 2 | 1 | 1 |
| December | Gainesville, FL | 30 | 7 | 4 | 3 |
| January | Gainesville, FL | 20 | 0 | | |

EXAMPLE 3

SINV-2-uninfected laboratory-reared monogyne colonies were identified by RT-PCR and divided into 4 equivalent fragment colonies comprised of about 0.5 grams of brood and about 4 ml of workers. Colonies were infected by a modified method described by Ackey and Beck (J. Insect. Physiol, Volume 18, 1901-1914, 1972), Workers and brood, approximately 0.15 gram, from a SINV-2-infected colony were homogenized in an equal volume of approximately 10% sucrose. The homogenate was filtered through 4 layers of cheesecloth. Approximately 4 ml of the homogenate/sucrose solution was placed into a cotton-stopped test tuve and presented to 3 of the 4 fragment colonies; one fragment colony was provided a homogenate of uninfected ants and served as control. After about 2 days, the homogenate was removed and replaced with unadulterated 10% sucrose, water, frozen crickets (*Acheta domesticus*) and egg yolk (hard boiled). Three replicates were conducted comprised of three colonies, each that had been fragmented into 4 subcolonies. Fragment colonies were examined by RT-PCR at 0,7,14,21,28, and 45 days after exposure to the homogenate.

Ice-chilled fire ant workers from a SINV-2-positive colony were placed on a glass slide, and head, thorax, and abdomen were separated with a surgical blade under a Leica MS5 dissecting microscope. The abdomen was immersed in 10 mM Tris-HCl, pH 8.0, and tissues were isolated and removed with micro-dissecting forceps in the following order: crop, poison sac, alimentary canal comprised of the midgut, hindgut, and Malpigian tubes; and the remaining abdomen carcass comprised of the Dufour's gland, ovary, fat body, muscle, and cuticle. Six replicates were conducted each comprised of body parts and tissues pooled from 5 workers. RNA was extracted from the body parts and tissues with Trizol reagent. The RNA concentration was measured spectrophotometricaly.

cDNA was synthesized from the SINV-2 genome region corresponding to an area between the helicase and RdRp with total RNA isolated from dissected tissues using SuperScript III Reverse Transcriptase (SsRT; Invitrogen) and a gene-specific primer, p514 (Table 1). In a 0.5 ml PCR tube, approximately 2 microliters of primer p514 (approximately 1 micromole), approximately 1 microliter of a dNTP mix (approximately 10 mM), and approximately 10 microliters of total RNA (approximately 100 ng) were mixed and heated to about 65 degrees C. for about 5 minutes in a PCR reaction machine, PTC 100 thermal cycler, followed by incubation on ice for about 1 minute. Then approximately 4 microliters of first-strand buffer, approximately 250 mM Tris-HCl, pH 8.3; Approximately 375 mM KCl, 15 mM $MgCl_2$), approximately 2.75 microliters of DEPC water, and approximately 0.25 microliters of SsRT (approximately 200 U/microliter) were added. The mixture was incubated at approximately 55 degrees centigrade for about 30 minutes, followed by inactivation of SsRT by heating to approximately 70 degrees centrigrade for about 15 minutes.

QPCR was performed on an automatic sequence detection system, ABI PRISM 7000 Sequence Detection System interfaced to sequencing software, the ABI PRISM 7000 SDS sortware (Applied Biosystems, Foster City, Calif.) in approximately a 25 microliter reaction volume. The reaction contained approximately 12.5 microliters of a conventional SYBR Green SuperMix with uraci -DNA- glycosylase, UDG and a red fluorescence dye, ROX (Invitrogen), approximately 0.4 microliters each of approximately 10 microM SINV-2-specific primers, p511, and p515, Table 1), approximately 3 mM $MgCl_2$, approximately 1 microliter of cDNA synthesis reaction, and approximately 10.7 microliters of DEPC-water. QPCR conditions consisted of one cycle at approximately 50 degrees C. for about 2 minutes and approximately 95 degrees C. for about 10 minutes, followed by about 40 cycles at approximately 95 degrees C. for about 15 seconds, approximately 72 degrees C. for about 1 minute. The non-template control for QPCR included a mock cDNA synthesis reaction that was carried out with RNA template. A standard curve was constructed from a plasmid clone of the corresponding SINV-2 genome region using a copy number range of approximately $5-5\times10^6$ copies per QPCR. Reaction efficiencies were determined by regressing $C_T$ values against the template copy number (log) and calculated according to the formula $[E=(10^{-1/10})-1]$ (Klein et al., Electrophoresis, Volume 20, 291-299,1999). Reaction efficiencies routinely exceeded approximately 95%.

Transmission of SINV-2 to uninfected *S. invicta* was successfully accomplished by feeding. SINV-2 was detectable in uninfected colonies within 7 days of exposure to a partially purified homogenate of SINV-2-infected fire ants (FIG. 4). The infection was detected for at least 45 days after treatment, indicating sustained infection among recipient colonies. The overwhelming majority (approximately 99%) of the viral genome copies were found in the alimentary canals of worker ants (Table 3).

TABLE 3

Distrubtuion of the SINV-2 genome among different tissues and body parts of *Solenopsis invicta* workers by RT-PCR and quantitative PCR.

| Tissue/body part | SINV-2 presence by RT-PCR | Distribution of SINV-2 genome (%)$_a$ |
|---|---|---|
| Head | + | 0.1 ± 0.01 |
| Thorax | + | 0.6 ± 1.4 |
| Crop | + | 0.1 ± 0.2 |
| Poison Sac | + | 0.1 ± 0.2 |
| Abdominal carcass | + | 0.1 ± 0.1 |
| Alimentary Canal | + | 99.0 ± 1.4 |

EXAMPLE 5

Blastp analysis was conducted with conserved regions of SINV-2 RdRp, helicase, and the N-terminal region of a putative structural protein (ORF1). Representative viruses exhibiting significant e-scores ($<10^{-5}$) were included in the phylogenetic analysis. Viral nucleotide sequences were retrieved from the genome resource at NCBI and used for comparative ORF analysis and multiple-alignment with SINV-2 usng advanced sequence analysis software, Vector NTI Advance software (Version 10.1.1, Invitrogen). Multiple alignments were carried out for the deduced amino acid sequences of the non-structural and structural polyproteins of viral genomes.

Specifically, conserved regions of the RdRp (domains-I-VIII), helicase (domains A, B, and C) and those corresponding t SINV-2 ORF 1 (a putative structural protein) were aligned and subsequently used to construct an unrooted radial phylogenetic tree using the neighbor-joining method (Saitou and Nei Mol. Biol. Evol., Volume 4, 406-425, 1987) in ClustalX (Thompson et al., Nucleic Acids Res., Volume 22, 4673-4680, 1994). The statistical significance of branch order was estimated by performing 1000 replicatins of bootstrap resampling of the original aligned amino acid sequences. Trees were generated with TreeView (Page, Computer Applications in the Biosciences, Volume 12, 357-358, 1996).

Figure 5A:
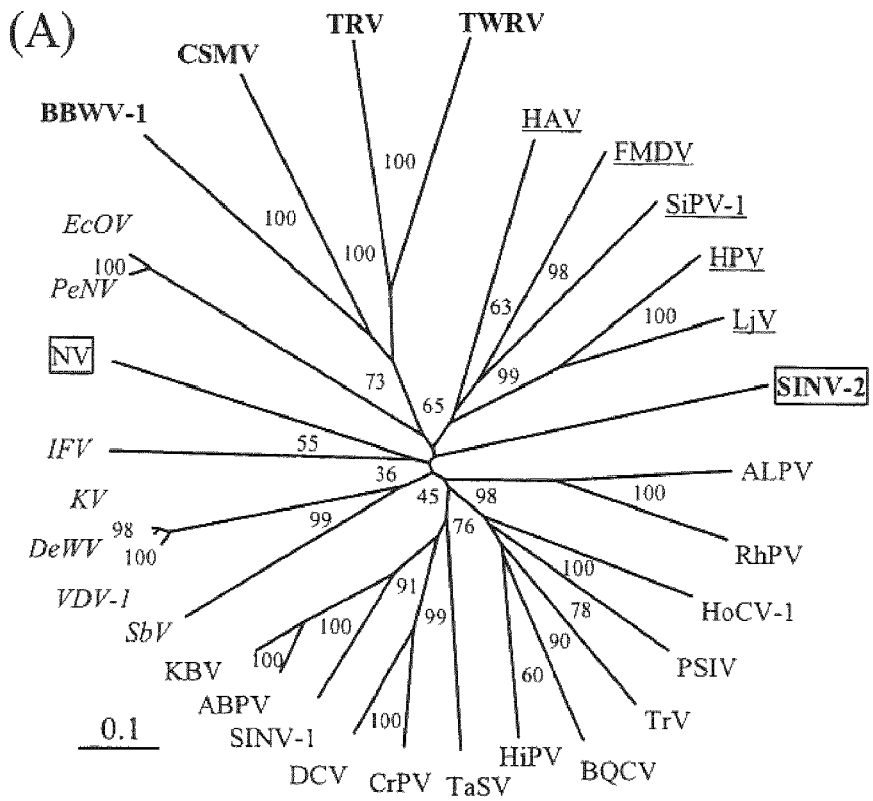
FIG. 5(A) is a chart of phylogenetic analysis of conserved amino acid sequences containing domains I to VIII of the putative RdRp from thirteen dicistroviruses, seven iflaviruses (italic), four plant RNA viruses (bold), five picornaviruses (underlined), Nora virus (boxed), and SINV-2 (bold and boxed).
Figure 5B:
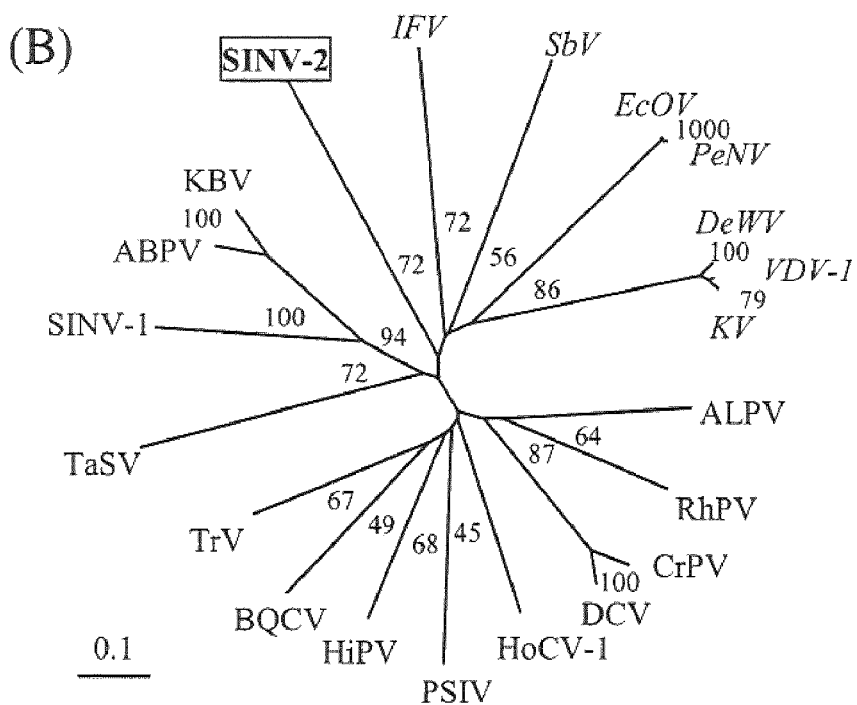
FIG. 5(B) is a chart of phylogenetic analysis of a domain of a putative structuaral protein form thirteen discistroviruses, seven iflaviruses (italic), and SINV-2 bold and boxed. Abbreviation of virus, accession number of the virus RNA or protein sequences, and amino acid residue numbers of aligned Sequences in a specific ORF (5' proximal and 3' proximal ORFs of dicistroviruses are used as non-structural and structural protein encoding sequences, respectively; otherwise an ORF number is specified) used to construct phylogenetic trees are: (A) Aphid lethal paralysis virus (ALPV) [AF536531], 1661-1955; Black queen cell virus (BQCV) [AF183905], 1415-1693; Cricket paralysis virus (CrPV) [AF218039], 1421-1699; Drosophila C virus (DCV) [AF014388], 1415-1693; Himetobi P virus (HiPV) [AB017037], 141-1710; Plautia stali intestine virus (PSIV), [A13006531], 1465-1739; Rhopalosiphum padi virus (RhPV) [AFO22937], 1625-1916; Triatoma virus (TrV) [AF178440], 1408-1682; Acute bee paralysis virus (ABPV), [AF150629], 1562-1837; Homalodisca coagulata virus-1 (HoCV-1) [DQ288865], 1446-1716; Kashmir bee virus (KBV) [AY275710], 1594-1864; Solenopsis invicta virus-1 (SINV-1) [AY6343,14], 1048-1327; Taura syndrome virus (TaSV) [AF277675], 1770-2036; Infectious flacherie virus (IFV) [AB000906], 2618-2888; Perina nuda virus (PeNV) [AF323747], 2628-2899; Sacbrood virus (SbV) [AF092924], 2518-2789; Deformed wing virus (DeWV) [AJ489744], 2556-2826; Ectropis oblique picorna-like virus (EcOV), [AY365064], 2629-2900; Kakugo virus (KV) [AB070959], 2556-2826; Varroa destructor virus-1 (VDV-1), [AY251269], 2556-2826; Foot-and-mouth disease virus O (FMDV) [AF308157], 2011-2264; Hepatitis A virus (HAV) [M14707], 1900-2159; Human parechovirus (HPV) [AJ005695], 1871-2117; Ljungan virus (LjV) [AF327920], 1945-2191; Simian picornavirus-1 (SiPV-1) [AY064708], 2119-2368; Broad bean wilt virus-1 (BVWV) [NP951930] RNA1, 405-657; Cowpea severe mosaic virus (CSMV) RNA-1 [M83830], 1553-1816; Tomato ringspot virus (TRV) [ABG23688] RNA1, 406-672; Tomato white ringspot virus (TWRV) [ABM65095], 1601-1872; Nora virus (NV) [DO321720] ORF2, 1763-2026; SINV-2 ORF4 [EF428566], 1810-2079; for FIG. 5B: ALPV, 89-228; BQCV, 720299; CrPV, 88-220; DCV, 67-199; HiPV, 8-138; PSIV, 133-263; RhPV, 5-141; TrV, 115-246; ABPV, 130-246; HoCV-1, 131-261; KBV, 86-220; SINV-1, 139-272; TaSV, 122-253; IFV, 252-388; PeNV, 416-553; SbV, 253-391; DeWV, 318-456; EcOV, 417-554; KV, 318-456; VDV-1, 318-456; SINV-2)RF1, 105-258.

Phylogenetic analysis of the RdRp domain placed SINV-2 IFV, and the Nora virus each standing alone, separated from clusters comprised of dicistroviruses, iflaviruses, picornaviruses, and plant small RNA viruses (FIG. 5A). Bootstrap values between the major clusters and SINV-2 were relatively low, suggesting an uncertain common ancestor. A similar positioning of SINV-2 was observed when the conserved region of the helicase (domains A, B, and C) was analyzed (Data not shown). When phylogenetic analysis was conducted using a conserved region identified from multiple alignments of SINV-2 ORF-1 and putative structural protein sequences of completely sequenced dicistroviurses and iflaviruses, both virus groups clustered independently, leaving SINV-2 isolated within the tree (FIG. 5B). Bootstrap values at nodes separating SINV-2 and neighboring clusteres were greater than 70%. This independent placement of SINV-2 corresponds, well with phylogenetic results from the RdRp and helicase which indicates a very early divergence of SINV-2 among the positive-strand RNA viruses.

The foregoing detailed description is for the purpose of illustration. Such detail is solely for that purpose and those skilled in the art can make variations without departing from the spirit and scope of the invention.

We claim:

1. A purified *Solenopsis invicta* virus 2 (SINV2) having SEQ ID NO: 1.

2. A biocontrol composition comprising:
   a. an effective amount of a *Solenopsis invicta* virus 2 (SINV2) preparation having SEQ ID NO: 1 to at least reduce the number of fire ants in a colony, and
   b. a carrier.

3. The composition of claim 2 wherein said carrier is a food source for said ants.

4. The composition of claim 3 wherein said food source is selected from the group consisting of insects, cooled egg yolk, corn cob grits, soybean oil, extruded corn pellets, and mixtures thereof.

5. A biocontrol composition comprising purified *Solenopsis invicta* virus 2 (SINV2) SINV 2 having SEQ ID NO: 1.

* * * * *